United States Patent [19]

Berg et al.

[11] 4,035,481
[45] July 12, 1977

[54] ANTIBIOTIC A-28086 AND PROCESS FOR PRODUCTION THEREOF

[75] Inventors: David H. Berg, Greenfield; Robert L. Hamill, Greenwood; Marvin M. Hoehn, Indianapolis, all of Ind.

[73] Assignee: Eli Lilly and Company, Indianapolis, Ind.

[21] Appl. No.: 685,033

[22] Filed: May 10, 1976

Related U.S. Application Data

[60] Division of Ser. No. 569,740, April 21, 1975, which is a continuation-in-part of Ser. No. 477,954, June 10, 1974, abandoned.

[51] Int. Cl.$^2$ .................................... A61K 35/00
[52] U.S. Cl. ............................... 424/122; 424/283
[58] Field of Search ........................... 424/122, 283

[56] References Cited

U.S. PATENT DOCUMENTS 3,857,948  12/1974  Tanaka et al. ................... 424/283

Primary Examiner—Jerome D. Goldberg
Attorney, Agent, or Firm—Nancy J. Harrison; Everet F. Smith

[57] ABSTRACT

Antibiotic A-28086 complex, comprising microbiologically active, structurally related factors A, B, and D, produced by submerged aerobic fermentation of Streptomyces aureofaciens NRRL 5758. Individual factors A, B, and D are separated and isolated by chromatography. The A-28086 antibiotics are antibacterial, antifungal, antiviral, anti-PPLO, anticoccidial, insecticidal and acaricidal agents and also increase feed-utilization efficiency in ruminants.

4 Claims, 7 Drawing Figures

INFRARED ABSORPTION SPECTRUM OF ANTIBIOTIC

A-28086 FACTOR A

ANTIBIOTIC A-28086 AND PROCESS FOR PRODUCTION THEREOF

This is a division of application Ser. No. 569,740 filed Apr. 21, 1975, which is a continuation-in-part of our application Ser. NO. 477,954, filed June 10, 1974, now abandoned.

BACKGROUND OF THE INVENTION

1. Field of the Invention

Although many antibacterial agents are known today, there continues to be a demand for new, improved antibiotics. One problem in current antibiotic therapy is the fact that antibiotics differ in their effectiveness against pathogenic organisms. Another problem is the development of organism strains which are resistant to standard antibiotics. Yet another problem is the fact that individual patients often suffer serious reactions to specific antibiotics, due to hypersensitivity and/or to toxic effects. Because of these problems in current therapy, new antibiotics continue to be in demand.

In addition to demands for new antibiotics which are useful in treating diseases in humans, improved antibiotics are also needed in the veterinary field. In one important aspect, improved antibiotics are needed to promote growth in poultry and in livestock. Growth promotion is achieved, for example, by reducing disease and by increasing feed-utilization efficiency.

One well-known disease of economic importance to veterinary science, more specifically to the poultry industry, is the protozoan disease coccidiosis. Coccidiosis results from infection by one or more species of Eimeria or Isospora (for a summary, see Lund and Farr in "Diseases of Poultry," 5th ed, Biester and Schwarte, Eds., Iowa State University Press, Ames, Ia., 1965, pp 1056–1096). In view of the great economic losses due to coccidiosis and the disadvantages of some known anticoccidial agents, the search for better anticoccidial agents continues.

Enteritis is another disease which can cause severe economic losses to livestock producers. Enteritis occurs in chickens, swine, cattle and sheep and is attributed mainly to anaerobic bacteria, particularly *Clostridium perfringens*, and viruses. *Enterotoxemia* in ruminants, and example of which is "overeating disease" in sheep, is a condition caused by *C. perfringens* infection.

Promotion of growth in ruminants, such as cattle, is another economically desirable objective of veterinary science. Of particular interest is growth promotion achieved by increasing feed-utilization efficiency. The mechanism for utilization of the major nutritive portion (carbohydrates) of ruminant feeds is well known. Micro-organisms in the rumen of the animal degrade carbohydrates to produce monosaccharides and then convert these monosaccharides to pyruvate compounds. Pyruvates are metabolized by microbiological processes to form acetates, butyrates or propionates, collectively known as volatile fatty acids (VFA). For a more detailed discussion, see Leng in "Physiology of Digestion and Metabolism in the Ruminant," Phillipson et al., Eds., Oriel Press, Newcastle-upon-Tyne, England, 1970, pp 408-410.

The relative efficiency of VFA utilization is discussed by McCullough in Feedstuffs, June 19, 1971, page 19; Eskeland et al. in J. An. Sci. 33, 282 (1971); and Church et al. in "Digestive Physiology and Nutrition of Ruminants," Vol. 2, 1971, pp 622 and 625. Although acetates and butyrates are utilized, propionates are utilized with greater efficiency. Furthermore, when too little propionate is available, animals may develop ketosis. A beneficial compound, therefore, stimulates animals to produce a higher proportion of propionates from carbohydrates, thereby increasing carbohydrate-utilization efficiency and also reducing the incidence of ketosis.

2. The Prior Art

Antibiotic A-28086 factors A, B, and D are new members of a group of polyether antibiotics. Examples of members of this group include monesin (U.S. Patent 3,501,568); dianemycin [R.. Hamill, M.M. Hoehn, G.E. Pittenger, J. Chamberlin, and M. Gorman, J. Antibiotics 22, 161 (1969)]; nigericin [L.K. Steinrauf, Mary Pinkerton, and J.W. Chamberlin, Biochem. Biophys. Res. Comm. 33 29 (1968)]and salinomycin [Japan patent publication 47-25392, dated Oct. 20, 1972, application number 19620/1971; Derwent No. 76960T, U.S. Pat. No. 3,857,948; and H. Kinashi, N. Otake, H. Yonehara, S. Sato and Y. Saito, Tetrahedron Lett. 49, 4955–4958 (1973)].

SUMMARY OF THE INVENTION

This invention relates to antibiotic substances. In particular, it relates to an antibiotic complex comprising at least three individual factors. The complex comprising individual factors A, B, and D is produced by culturing a hitherto undescribed strain of the organism *Streptomyces aureofaciens* Duggar, NRRl 5758.

The term "antibiotic complex" as used in the fermentation art and in this specification does not refer to a chemical complex, but to a mixture of co-produced individual antibiotic factors. As will be recognized by those familiar with antibiotic production by fermentation, the ratio of individual factors produced in an antibiotic complex will vary, depending on the fermentation conditions used.

The antibiotic substances in this invention are arbitrarily designated herein as A-28086 antibiotics. The two individual antibiotics of the present invention are designated antibiotic A-28086 factors A and B. The $C_2$–$C_6$-acyl ester derivatives of A-28086 factor A and the physiologically-acceptable salts of said ester derivatives and of A-28086 factors A and B are also part of this invention. The A-28086 antibiotic complex also contains individual factor D which is the subject of a separate invention. To simplify discussions of utility, the term "A-28086 compound" is used and refers to individual factors A and B, the specified acyl ester derivatives of factor A or physiologically-acceptable salts as above defined. A-28026 factor D has an activity pattern similar to that of A-28086 factors A and B.

The A-28086 antibiotic complex is produced by culturing the novel strain of *Streptomyces auerofaciens* NRRL 5758 under submerged aerobic fermentation conditions until a substantial level of antibiotic activity is produced. The A-28086 antibiotic complex can also be produced by culturing yet another novel strain of *Steptomyces aureofaciens*, NRRL 8092. When produced by either *S. aureofaciens* NRRL 5758 or by *S. aureofaciens* NRRL 8092, the A-28086 antibiotic complex is extracted from the fermentation broth and from the mycelium with polar organic solvents. The extracted antibiotic mixture is separated by concentrating the solvents, adding the concentrates to excesses of petroleum ether to precipitate impurities, filtering, and evaporating the filtrates to obtain the A-28086 antibiotic mixture. The antibiotic mixture is further purified and separated into individual factors by column chromatography.

The A-28086 compounds of this invention inhibit the growth of organisms which are pathogenic to animal and plant life. In one aspect of this inhibitory activity, the A-28086 compounds are anticoccidial agents. In addition, the A-28086 compounds are antibacterial, antifungal, antiviral, anti-PPLO, insecticidal and acaricidal agents and increase feed-utilization efficiency in ruminants.

DESCRIPTION OF THE DRAWINGS

The following infrared absorption spectra in chloroform are presented in the drawings.

DETAILED DESCRIPTION OF THE INVENTION

The A-28086 factors of this invention are structurally related to each other. At least four antibiotic factors are coproduced during the fermentation and are obtained as a mixture. The factors are separated from each other, and factors A, B, and D are isolated as individual compounds as hereinafter described. The mixture of A-28086 factors is soluble in most organic solvents, but is insoluble in water.

The following paragraphs describe the physical and spectral properties of A-28086 factors A and B, the two factors of the present invention.

Antibiotic A-28086 factor A crystallizes from acetone-water. A-28086 factor A melts at about 98°–100° C., resolidifies and remelts at about 195°–200° C. Elemental analysis of factor A gave the following average percentage composition: carbon, 66.69 percent; hydrogen, 9.85 percent; oxygen, 23.10 percent. The empirical formual proposed for factor A is $C_{43}H_{72}O_{11}$.

Factor A has an apparent molecular weight of 764 as determined by mass spectrometry.

Figure 1:
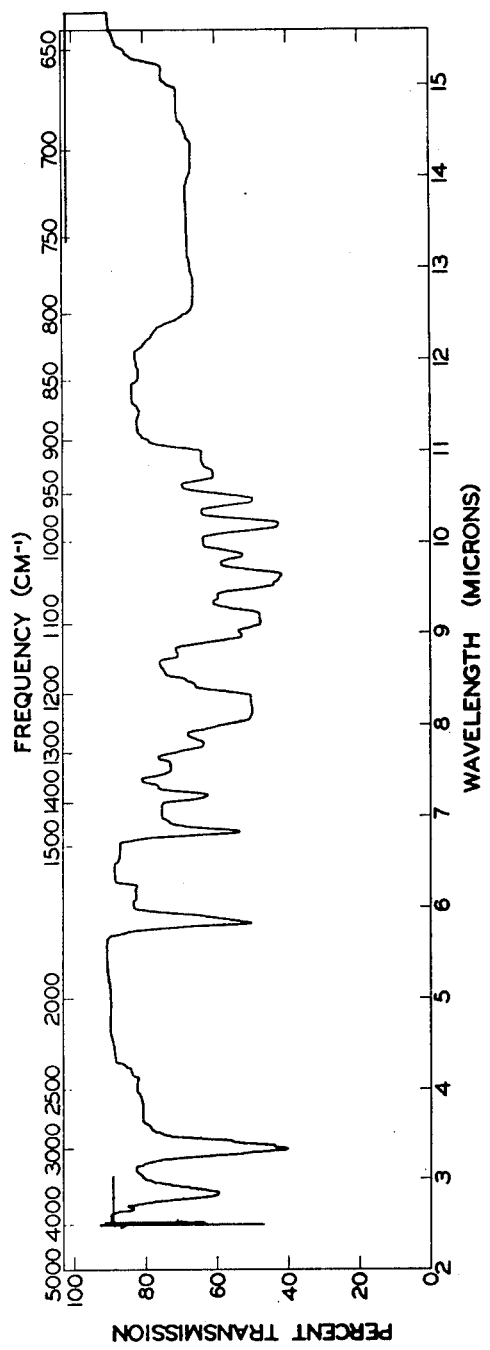
FIG. 1 - Antibiotic A-28086 factor A

The infrared spectrum of factor A in chloroform is shown in FIG. 1 of the accompanying drawings. The following absorption maxima are observed: 2.85, 3.34, 5.83, 6,82, 7.22, 7.53 (weak), 7.78 (weak), 8.75 (strong), 8.95 (strong), 9.15, 9.50 (strong), 9.55 (strong), 9.60, 9.85, 10.15, 10.45, and 10.70 (weak) microns.

The ultraviolet spectrum of factor A in ethanol shows only end absorption below 220 m$\mu$.

The nuclear magnetic resonance spectrum of A-28086 factor A in deuterochloroform showed the following characteristics: $\delta$ 6.01, 4.21, 4.11, 3.99, 3.89, 3.80, 3.67, 3.65, 3.57, 3.55, 2.83, 2.76, 2.74, 2.68, 2.66, 2.58, 2.56, 2.30, 2.22, 2.17, 2.10, 2.05, 1.96, 1.90, 1.85, 1.70, 1.62, 1.60, 1.47, 1.39, 1.31, 1.25, 1.18, 0.95, 0.93, 0.90, 0.88, 0.85, 0.77, 0.75, 0.73, 0.68, and 0.66 ppm.

Antibiotic A-28086 factor a, crystallized from acetone-water, has the following characteristic X-ray powder diffraction pattern (Cu $^{++}$ radiation, 1.5405$\lambda$, nickel filter, $d =$ interplanar spacing in angstroms):

| d | Relative Intensity |
| --- | --- |
| 12.00 | 100 |
| 10.10 | 50 |
| 9.25 | 90 |
| 8.00 | 40 |
| 7.50 | 15 |
| 6.92 | 90 |
| 6.40 | 40 |
| 5.98 | 05 |
| 5.68 | 15 |
| 5.20 | 40 |
| 4.98 | 40 |
| 4.62 | 40 |
| 4.21 | 20 |
| 3.48 | 10 |

The specific rotation of antibiotic A-28086 factor A is $-54°$ (c=0.2, methanol), when determined at a temperature of 25°C. This specific rotation is an average value, based on several determinations.

Electometric titration of factor A in 80% aqueous dimethylformamide indicated the presence of a titratable group with a p$K_a$ value of 7.9.

Antibiotic A-28086 factor A is soluble in a variety of organic solvents such as methanol, ethanol, dimethylformamide, dimethyl sulfoxide, ethyl acetate, chloroform, acetone, and benzene; but is only slightly soluble in nonpolar organic solvents such as hexane; and is insoluble in water.

Antibiotic A-28086 factor A has an acid function capable of forming salts and ester derivatives and at least one hydroxyl group capable of esterification.

Based on the physical characteristics hereinabove recited, a structure for antibiotic A-28086 factor A can be proposed. Since the structure determination is merely postulated, however, it is to be understood that the structure presented herein represents merely a working hypothesis. The tentative structure for A-28086 factor A is shown in Formula I:

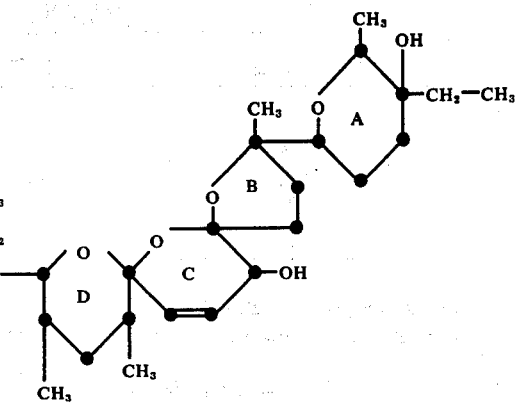
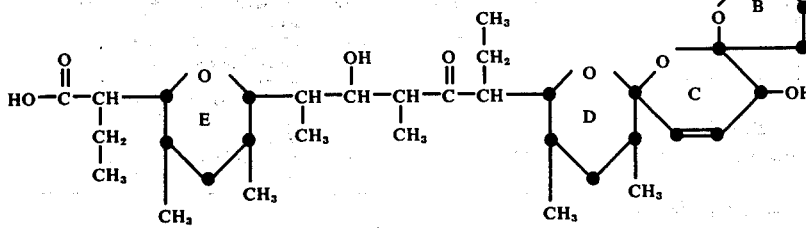

I

Antibiotic A-28086 factor B is a white crystalline compound (from acetone-water) which has a melting point of about 150°–153° C.

As determined by high-resolution mass spectrometry, factor B has an apparent molecular weight of 762 and a proposed empirical formula of $C_{43}H_{70}O_{11}$.

Figure 2:
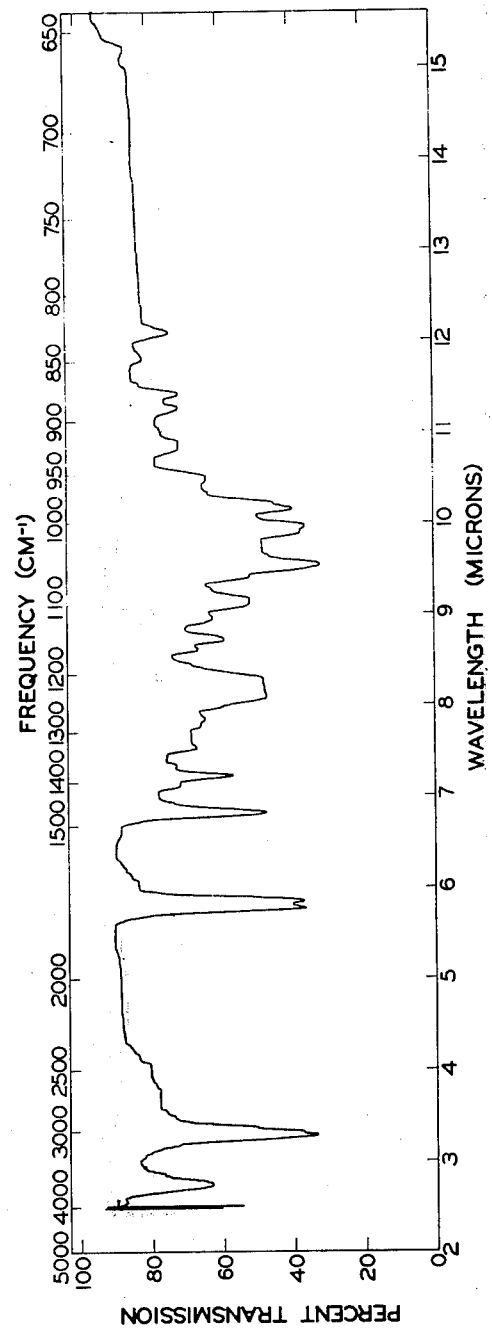
FIG. 2 - Antibiotic A-28086 factor B

The infrared spectrum of factor B in chloroform is shown in FIG. 2 of the accompanying drawings. The following absorption maxima are observed: 2.82, 3.30, 5.77, 5.85, 6.80, 7.20, 7.50 (weak), 7.72 (weak), 7.80 (weak), 8.57 (strong), 8.68, 8.90, (strong), 9.10, 9.50, 9.83 (strong), 9.90, 10.10, 10.17 (strong), 10.43 (weak), 10.80 (weak), 11.20 (weak), 11.35 (weak), 11.73 (weak), and 12.03 (weak) microns.

The ultraviolet spectrum of factor B in ethanol shows an absorption maximum at 220 m$\mu$ ($E_{1cm}^{1\%} = 137.5$; $\epsilon=10,477$).

The nuclear magnetic resonance spectrum of A-28086 factor B in deuterochloroform showed the following characteristics: $\delta$ 7.20, 7.09, 6.26, 6.15, 4.19, 4.12, 4.05, 3.95, 3.89, 3.78, 3.62, 3.59, 3.52, 3.48, 2.81, 2.73, 2.63, 2.54, 2.52, 1.99, 1.91, 1.84, 1.71, 1.67, 1.64, 1.55, 1.43, 1.33, 1.18 1.11, 0.96, 0.94, 0.90, 0.87, 0.84, 0.77, 0.74, and 0.68 ppm.

Antibiotic A-28086 factor B is soluble in a variety of organic solvents such as, for example, methanol, ethanol, dimethylformamide, dimethyl sulfoxide, ethyl acetate, chloroform, acetone and benzene; but is only slightly soluble in nonpolar organic solvents such as hexane; and is insoluble in water.

Although the chemical structure of A-28086 antibiotic factor B has not been elucidated, the physical-chemical data thus far available indicate that factor B has a single carboxylic acid moiety, two keton moieties, and one or more hydroxyl moieties.

Antibiotic A-28086 factor D, when produced by *S. aureofaciens* NRRL 5758, is a minor factor. When produced by *S. aureofaciens* NRRL 8092, however, A-28086 factor D is present in amounts up to 10% of the recovered antibiotic activity. Antibiotic A-28086 factor D is the subject of a copending application of Nakatsukasa and Hamill, titled ANTIBIOTIC A-28086 FACTOR D AND PROCESS FOR PRODUCTION THEREOF, Ser. No. 569,719, filed this even date herewith.

The following paragraphs described the physical and spectral properties of antibiotic A-28086 factor D.

Antibiotic A-28086 factor D is a white crystalline material (from water-acetone) with a melting point of about 96°–98° C. A-28086 factor D has an apparent molecular weight of 778, as determined by high-resolution mass spectrometry.

The elemental composition of the peak in the mass spectrum of the sodium salt of A-28086 factor D was observed to be 800.5050 (Calcd for $C_{44}H_{73}O_{11}Na = 800.5050$). In the mass spectrum of A-28086 factor D free acid, a small peak at 778 and a larger peak at 760.5117 (Calcd for $C_{44}H_{72}O_{10} = 760.5125$) were observed. The m/e 760 in the mass spectrum of the free acid results from the loss of water from the molecular ion. The molecular-ion composition of A-28086 factor D free acid is, therefore, $C_{44}H_{74}O_{11}$.

The empirical formula proposed for A-28086 factor D is $C_{44}H_{74}O_{11}$. Elemental analysis of factor D gave the following percentage composition: carbon, 67.59 percent; hydrogen 9.38 percent; oxygen, 22.77 percent.

The theoretical percentage composition for $C_{44}H_{74}O_{11}$ is: carbon, 67.87 percent; hydrogen, 9.51 percent; oxygen, 22.77 percent.

The infrared absorption spectrum of A-28086 factor D contains the following observable absorption maxima: 2.89, 3.39, 3.43, 3.50, 5.88, 6.90, 7.27, 7.60, 7.84, 9.00, 9.26, 9.62, 10.31, 10.58, 11.10, and 11.49 microns.

A-28086 factor D in 95 percent aqueous ethanol shows no ultraviolet absorption.

The nuclear magnetic resonance spectrum of A-28086 factor D in deuterochloroform showed the following characteristics: $\delta$ 6.00, 4.20, 4.10, 4.00, 3.98, 3.92, 3.86, 3.83, 3.79, 3.67, 3.64, 3.57, 3.54, 2.88, 2.81, 2.71, 2.62, 2.58, 2.48, 2.43, 2.37, 2.29, 2.21, 2.15, 2.10, 2.04, 1.97, 1.89, 1.83, 1.76, 1.68, 1.61, 1.58, 1.55, 1.47, 1.39, 1.30, 1.25, 1.18, 0.95, 0.90, 0.88, 0.84, 0.74, and 0.68 ppm.

Antibiotic A-28086 factor D, crystallized from acetone-water, has the following characteristic X-ray powder-diffraction pattern (Cu$^{++}$radiation 1.5405λ, nickel filter, d = interplanar spacing in angstroms):

| d | Relative Intensity |
|---|---|
| 12.40 | 100 |
| 10.20 | 70 |
| 8.85 | 90 |
| 7.80 | 30 |
| 6.80 | 10 |
| 6.30 | 100 |
| 5.70 | 20 |
| 5.35 | 20 |
| 5.10 | 20 |
| 4.90 | 10 |

| d | Relative Intensity |
|---|---|
| 4.65 | 20 |
| 4.45 | 40 |
| 4.20 | 30 |
| 3.30 | 10 |
| 3.15 | 10 |
| 2.99 | 05 |
| 2.77 | 05 |
| 2.28 | 05 |

The specific rotation of antibiotic A-28086 factor D is −56° (c = 0.1, methanol), when determined at a temperature of 25° C.

Electrometric titration of A-28086 factor D in 80 percent aqueous dimethylformamide indicated the presence of a titratable group with a $pK_a$ value of 8.67.

Antibiotic A-28086 factor D is soluble in a variety of organic solvents such as methanol, ethanol, dimethylformamide, dimethyl sulfoxide, ethyl acetate, chloroform, acetone and benzene. A-28086 factor D is only slightly soluble in nonpolar organic solvents such as hexane and is insoluble in water.

Antibiotic A-28086 factor D has an acid function capable of forming salts and ester derivatives and at least one hydroxyl group capable of esterification.

Based on the physical characteristics hereinabove recited, a structure for antibiotic A-28086 factor D can be proposed. Since the structure determination is merely postulated, however, it is to be understood that the structure presented herein represents merely a working hypothesis. The tentative structure for A-28086 factor D is shown in Formula II:

TABLE I-continued

| $R_f$ Value | | | |
|---|---|---|---|
| Factor A | Factor B | Factor D | Solvent System |
| 0.54 | 0.46 | 0.36 | Water:methanol:acetone (12:3:1)-adjusted to pH 10.5 with $NH_4OH$ and then lowered to pH 7.5 with $H_3PO_4$ |
| 0.48 | 0.36 | 0.29 | 1% MIBK, 0.5% $NH_4OH$ in water |
| 0.15 | 0.33 | 0.25 | 17.4 g $K_2HPO_4$, 30 ml ethanol per liter of water |
| 0.24 | 0.51 | 0.26 | Benzene saturated with water |
| 0.24 | 0.11 | 0.09 | Water |
| 0.75 | 0.61 | 0.64 | Water:MIBK:ethyl acetate (98:1:1) |

In Table II are given the $R_f$ values for antibiotic A-28086 factors A, B and D in two thin-layer-chromatographic systems on silica gel (precoated plates, E. Merck, Darmstadt, F-254, layer thickness 0.25 mm), again using B. subtilis ATCC 6633 as a detection organism.

TABLE II

| $R_f$ Values | | | |
|---|---|---|---|
| Factor A | Factor B | Factor D | Solvent System |
| 0.24 | 0.42 | 0.26 | Benzene-ethyl acetate (3:2) |
| 0.54 | 0.34 | 0.66 | Ethyl acetate-diethylamine (95:5) |

Another substance, arbitrarily designated as A-28086-I, is co-produced with the antibiotic A-28086 complex. Although A-28086-I is not microbiologically

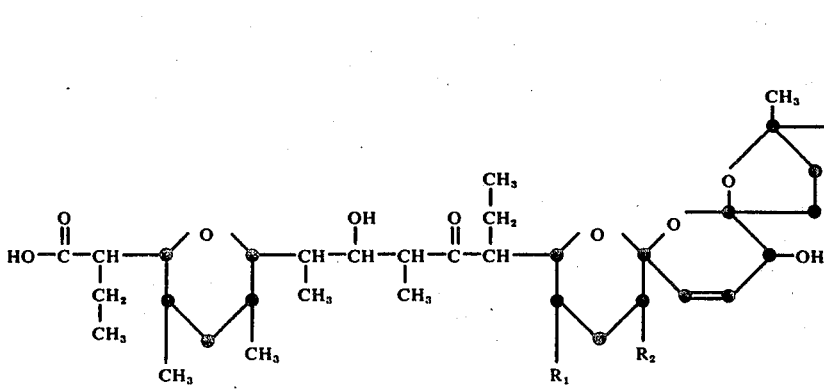

II wherein either:
$R_1 = CH_3$ and $R_2 = C_2H_5$
or:
$R_1 = C_2H_5$ and $R_2 = CH_3$ The $R_f$ values of antibiotic A-28086 factors A, B and D in various paper-chromatographic systems, using Bacillus subtilis ATCC 6633 as a detection organism, are given in Table I.

TABLE I

| $R_f$ Value | | | |
|---|---|---|---|
| Factor A | Factor B | Factor D | Solvent System |
| 0.11 | 0.09 | 0.10 | Water saturated with methyl isobutyl ketone (MIBK) |
| 0.41 | 0.16 | 0.26 | Water saturated with MIBK plus 2% p-toluenesulfonic acid and 1% piperidine | active, it is structurally related to the A-28086 antibiotic factors. A-28086-I is a white crystalline compound (from acetone-water) and has a melting point of about 160°–162° C. Comparative studies of the NMR spectra and other properties of A-28086-I and synthetically-prepared A-28086 factor A methyl ester give evidence that A-28086-I is the methyl ester of A-28086 factor A or a closely related compound such as a stereoisomer.

Although A-28086-I initially co-precipitates with the active A-28086 antibiotic factors, it is readily separated from them by silica gel chromatography. A-28086-I has an approximate $R_f$ value of 0.53 on silica gel thin-layer chromatography with ethyl acetate as the eluting solvent and using vanillin spray reagent (3% vanillin in methanol + 0.5 ml conc $H_2SO_4$ per 100 ml of solution) for detection. After spraying with vanillin and heating, A-28086-1 gives a blue spot while the A-28086 antibiotic factors give bright pink spots which quickly turn dark brownish-blue.

Antibiotic A-28086 factors A and B and the specified acyl ester derivatives of factor A are capable of forming salts. The physiologically-acceptable alkali-metal, alkaline-earth-metal and amine salts of antibiotic A-28086 factors A and B and the $C_2$—$C_6$-acyl ester derivatives of factor A are also part of this invention. "Physiologically-acceptable" salts are salts which are also pharmaceutically acceptable, that is, salts in which the toxicity of the compound as a whole toward warm-blooded animals is not increased relative to the non-salt form. Representative and suitable alkali-metal and alkaline-earth-metal salts of A-28086 factors A and B include the sodium, potassium, lithium, cesium, rubidium, barium, calcium, and magnesium salts. Suitable amine salts of A-28086 factors A and B include the ammonium and the primary, secondary and tertiary $C_1$-$C_4$-alkylammonium and hydroxy-$C_2$-$C_4$-alkylammonium salts. Illustrative amine salts include those formed by reaction of A-28086 factors A and B with ammonium hydroxide, methylamine, sec-butylamine, isopropylamine, diethylamine, diisopropylamine, ethanolamine, triethylamine, 3-amino-1-propanol and the like.

The alkali-metal and alkaline-earth-metal cationic salts of A-28086 factors A and B and of the factor A acyl ester derivatives are prepared according to procedures commonly employed for the preparation of cationic salts. For example, the free acid form of the antibiotic factor or ester derivative is dissolved in a suitable solvent such as warm methanol or ethanol; a solution containing the stoichiometric quantity of the desired inorganic base in aqueous methanol is added to this solution. The salt thus formed can be isolated by routine methods, such as filtration or evaporation of the solvent.

The salts formed with organic amines can be prepared in a similar manner. For example, the gaseous or liquid amine can be added to a solution of the antibiotic factor in a suitable solution such as acetone, and the solvent and excess amine can be removed by evaporation.

It is well known in the veterinary pharmaceutical art that the form of an antibotic is not significant when treating an animal with the antibiotic. In most cases, conditions within the animal change the drug to forms other than the form in which it was administered. The salt form in which it may be administered is, therefore, insignificant to the method of treatment. The salt form may, however, be chosen for reasons of economics, convenience, and toxicity.

A-28086 factor A forms acyl ester derivatives. Esterification occurs at one of the hydroxyl groups of A-28086 factor A upon treatment with a $C_2$-$C_6$-acid anhydride or acid chloride. Such esters are typically prepared by reacting A-28086 factor A with, for example, the corresponding acid anhydride at room temperature. These ester derivatives are also useful as antibiotics and as agents which increase feed-utilization efficiency.

The following paragraphs describe the characteristics of these A-28086-factor A acyl ester derivatives.

A-28086 factor A acetyl ester derivative is a white crystalline compound (from acetone-water) with a melting point of about 100°–103° C. A-28086 factor A acetyl ester derivative has an empirical formula of $C_{45}H_{74}O_{12}$ and a molecular weight of about 807, based on the empirical formula proposed for A-28086 factor A. Elemental analysis of factor A acetyl ester derivative gave the following percentage composition:

Calcd. for $C_{45}H_{74}O_{12}$: C, 66.97; H, 9.24; O, 23.79. Found: C, 67.67; H, 8.71; O, 23.13.

Figure 3:
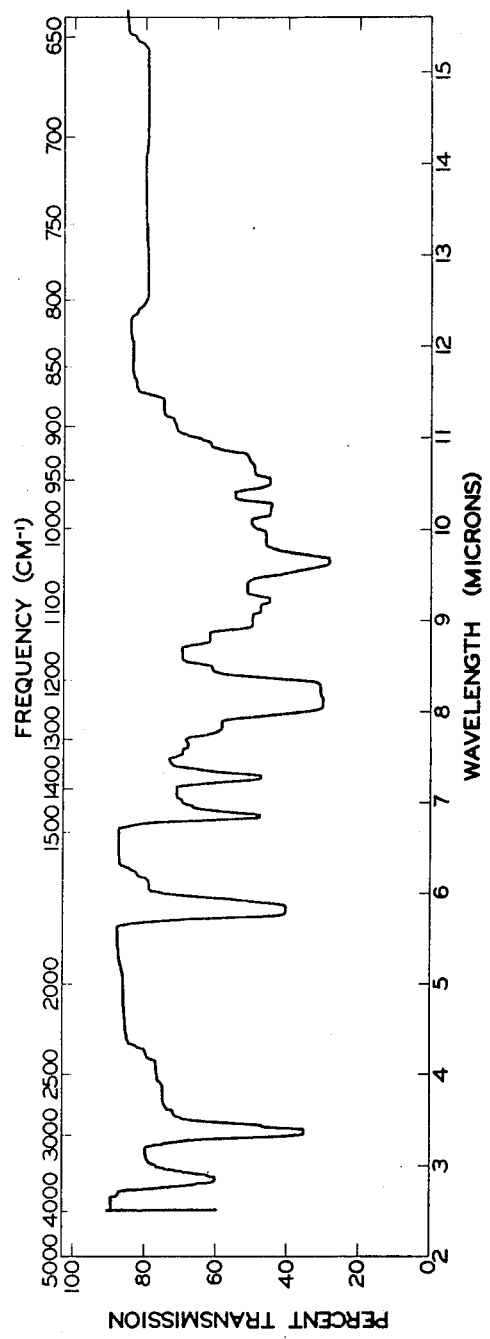
FIG. 3 - Antibiotic A-28086 factor A acetyl ester derivative

The infrared spectrum of A-28086 factor A acetyl ester derivative in chloroform is shown in FIG. 3 of the accompanying drawings. The following absorption maxima are observed: 2.85, 3.36, 3.38 (strong), 5.80, 6.83, 7.25, 7.52 (strong), 7.60 (weak), 7.80 (strong), 8.45 (strong), 8.80 (strong), 8.95 (strong), 9.10 (strong), 9.20, 9.63, 9.80 (strong), 10.12 (weak), 10.25 (weak), and 10.50 microns.

The ultraviolet spectrum of A-28086 factor A acetyl ester in ethanol shows only end absorption.

Electrometric titration of A-28086 factor A acetyl ester derivative in 80% aqueous dimethylformamide indicated the presence of a titratable group with a $pK_a$ value of 8.5.

A-28086 factor A propionyl ester derivative is a white crystalline compound (from acetone-water) with a melting point of about 96°–98° C. A-28086 factor A propionyl ester derivative has an empirical formula of $C_{46}H_{76}O_{12}$ and a molecular weight of about 821, based on the empirical formula proposed for A-28086 factor A. Elemental analysis of factor A propionyl ester derivative gave the following percentage composition:

Calcd for $C_{46}H_{76}O_{12}$: C, 67.29; H, 9.33; O, 23.38; Found: C, 66.06; H, 9.17; O, 23.41.

Figure 4:
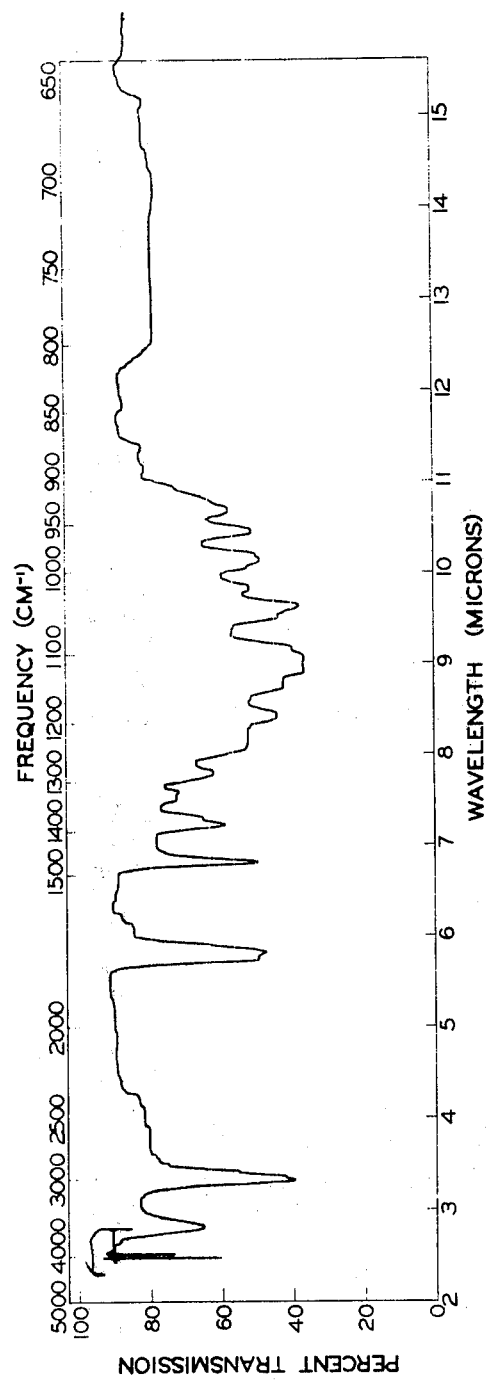
FIG. 4 - Antibiotic A-28086 factor A propionyl ester derivative

The infrared spectrum of A-28086 factor A propionyl ester derivative in chloroform is shown in FIG. 4 of the accompanying drawings. The following absorption maxima are observed: 2.85, 3.33, 3.38 (strong), 3.45 (strong), 5.75 (strong), 5.82, 6.81, 7.22, 7.30 (strong), 7.50 (weak), 7.60 (weak), 7.80, 8.43, 8.75 (strong), 8.90, 9.05, 9.15 (strong), 9.50 (strong), 9.63, 9.83 (weak), 10.05 (strong), 10.13, 10.20 (strong), 10.45, and 10.68 microns.

The ultraviolet spectrum of A-28086 factor A propionyl ester derivative in ethanol shows only end absorption.

Antibiotic A-28086 factor A butyryl ester derivative is a white crystalline compound (from acetone-water) with a melting point of about 96°–98° C. A-28086 factor A butyryl ester derivative has an empirical formula of $C_{47}H_{78}O_{12}$, a molecular weight of about 835, and an approximate composition of C, 67.60%; H, 9.41%; O, 22.99%, as derived from the empirical formula proposed for A-28086 factor A.

Figure 5:
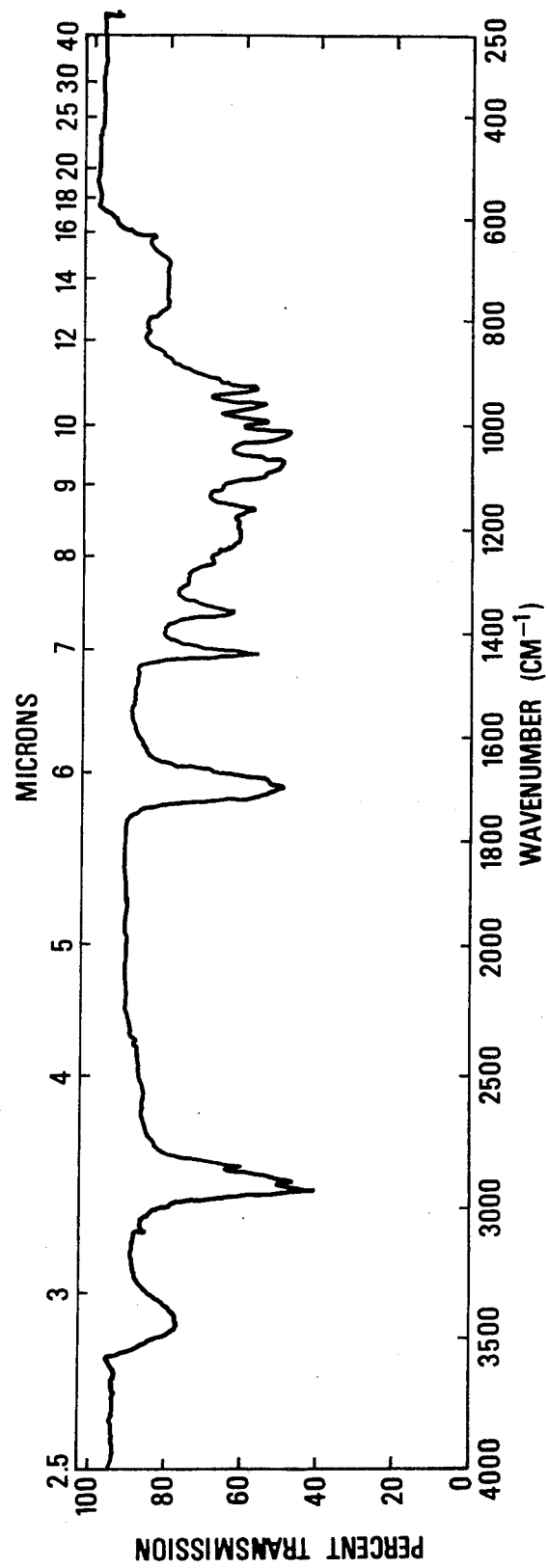
FIG. 5 - Antibiotic A-28086 factor A butyryl ester derivative

The infrared spectrum of A-28086 factor A butyryl ester derivative in chloroform is shown in FIG. 5 of the accompanying drawings. The following absorption maxima are observed: 2.89, 3.40, 3.45, 3.51, 5.85, 5.92 (strong), 5.97 (strong), 6.90, 7.30, 7.84 (weak), 8.55, 8.85 (weak), 9.01 (strong), 9.26, 9.76, 9.95, 10.31, and 10.64 microns.

Antibiotic A-28086 factor A valeryl ester derivative is a white crystalline compound (from acetone-water) with a melting point of about 173°–175° C. A-28086 factor A valeryl ester derivative has an empirical formula of $C_{48}H_{80}O_{12}$, a molecular weight of about 849, and an approximate composition of C, 67.89%; H, 9.50%; O22.61%, as derived from the empirical formula proposed for A-28086 factor A.

Figure 6:
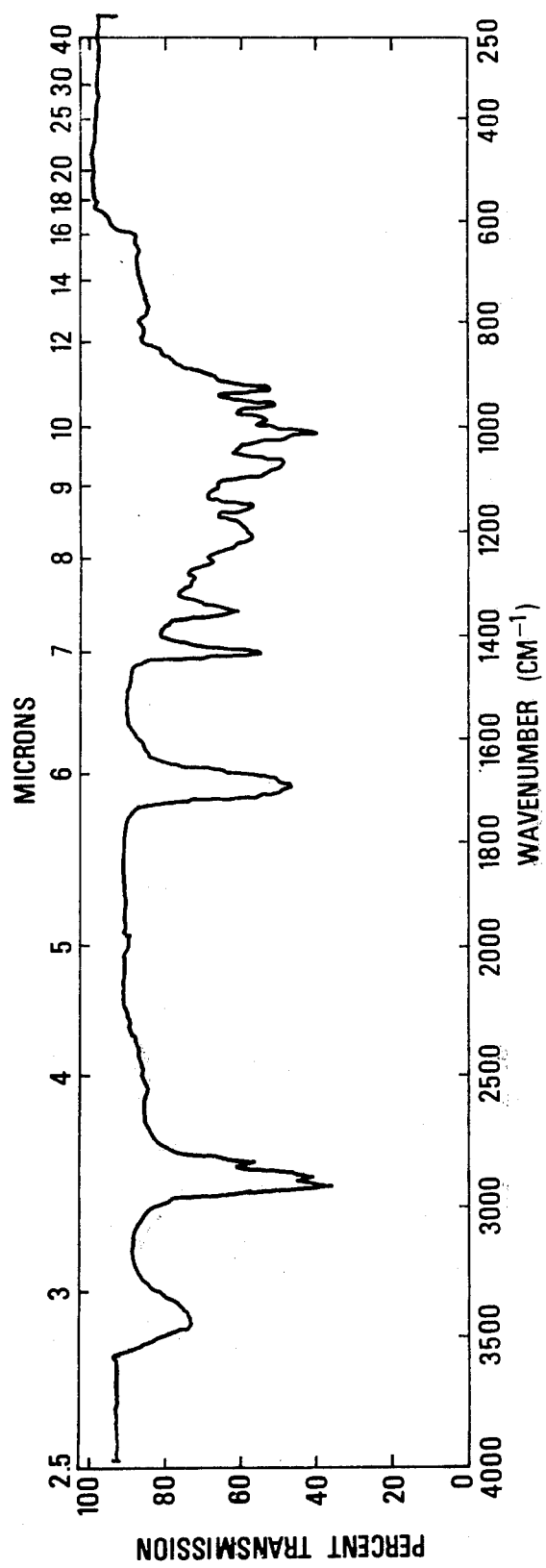
FIG. 6 - Antibiotic A-28086 factor A valeryl ester derivative

The infrared spectrum of A-28086 factor A valeryl ester derivative in chloroform is shown in FIG. 6 of the accompanying drawings. The following absorption maxima are observed: 2.90, 3.40, 3.45, 3.51, 5.87, 5.92

(strong), 5.99 (strong), 6.91, 7.30, 7.69 (weak), 7.87 (weak), 8.16, 8.58, 8.85 (weak), 9.26, 9.76, 10.00 (weak), 10.31, and 10.64 microns.

Antibiotic A-28086 factor A caproyl ester derivative is a white crystalline compound (from acetone-water) with a melting point of about 163°–167° C. A-28086 factor A capropyl ester derivative has an empirical formula of $C_{49}H_{82}O_{12}$, a molecular weight of about 863, and an approximate composition of C, 68.18%; H, 9.58%; O, 22.24%, as derived from the empirical formula proposed for A-28086 factor A.

Figure 7:
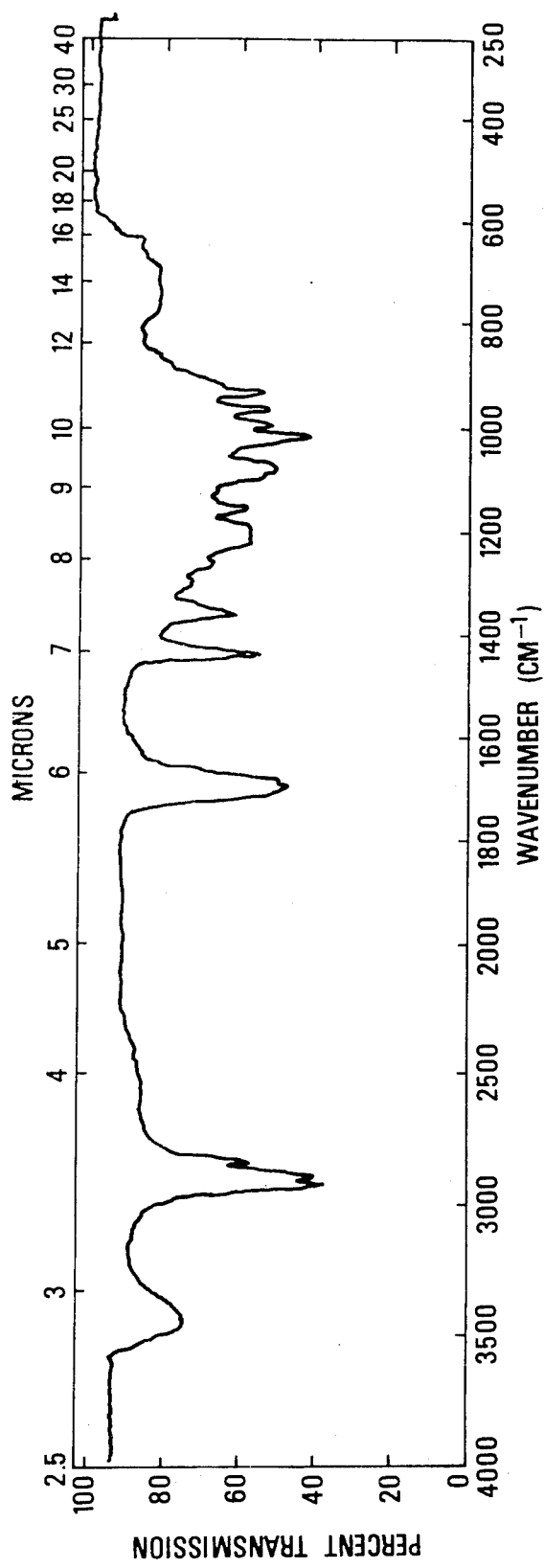
FIG. 7 - Antibiotic A-28086 factor A caproyl ester derivative

The infrared spectrum of A-28086 factor A caproyl ester derivative in chloroform is shown in FIG. 7 of the accompanying drawings. The following absorption maxima are observed: 2.90, 3.40, 3.45, 3.51, 5.87, 5.92 (strong), 5.97 (strong), 6.90, 7.30, 7.66 (weak), 7.84 (weak), 8.16, 8.58, 8.85 (weak), 9.05 (strong), 9.17, 9.72, 9.95, 10.29, and 10.62 microns.

Acylation of A-28086 factor A results in the following changes in the $^1$H nuclear magnetic resonance spectrum: the carbinyl resonance occurring at about 4 ppm is shifted downfield to approximately 5.3 ppm (the exact position varies slightly in the various acyl derivatives), and the vinyl-proton signals are also shifted. This is characteristic of the change represented in partial structure by:

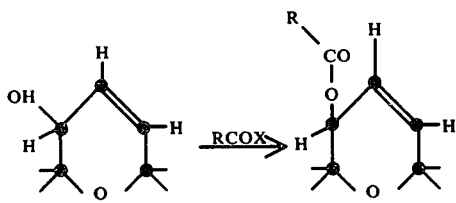

wherein R represents $C_1$–$C_5$-alkyl. This partial structure is in full accord with $^1$H homonuclear decoupling experiments and $^{13}$C nuclear magnetic evidence from the acetyl and propionyl ester derivatives.

The $C_2$–$C_6$-acyl ester derivatives of A-28086 factor A are soluble in a variety of organic solvents such as methanol, ethanol, dimethylformamide, dimethyl sulfoxide, ethyl acetate, chloroform, acetone, and benzene; but are only slightly soluble in nonpolar organic solvents such as hexane; and are insoluble in water.

Each of the $C_2$–$C_6$-acyl ester derivatives of A-28086 has an acid function capable of forming salts and ester derivatives.

The novel antibiotics of this invention are produced by culturing an A-28086-producing strain of *Streptomyces aureofaciens* under submerged aerobic conditions in a suitable culture medium until substantial antibiotic activity is produced. The antibiotics are recovered by employing various isolation and purification procedures commonly used and understood in the art.

One of the new organisms useful for the preparation of A-28086 antibiotics was isolated from a soil sample collected on Mount Ararat in Turkey. This organism is classified as a strain of *Streptomyces aureofaciens* Duggar, as described by E. B. Shirling and D. Gottlieb in "Cooperative Description of Type Cultures of *Streptomyces*. III. Additional Species Descriptions from First and Second Studies," *Intern. Bull. Systematic Bacteriol.* 18, 279–392 (1968). This classification is based on methods recommended for the International *Streptomyces* Project [E. B. Shirling and D. Gottlieb, "Methods for Characterization of *Streptomyces* species," *Intern. Bull. Systematic Bacteriol.* 16, 313–340 (1966)] along with certain supplementary tests. Color names were assigned according to the ISCC-NBS method (K. L. Kelly and D. B. Judd, "The ISCC-NBS Method of Designating Color and a Dictionary of Color Names," U.S. Dept. of Commerce, Circ. 553, 1955, Washington, D.C.). Figures in parentheses refer to the Tresner and Backus color series [Tresner, H. D. And S. J. Backus, "System of Color Wheels for *Streptomyces* Taxonomy," *Appl. Microbiol.* 11, 335–338 (1963)]; color tab designations are underlined. The Maerz and Paul color blocks (A. Maerz and M. R. Paul, "Dictionary of Color," McGraw-Hill Book Co., Inc., New York, N.Y., 1950) are enclosed in brackets. Cultures were grown at 30° C. for 14 days unless otherwise noted.

CHARACTERIZATION OF A-28086-PRODUCING STRAIN NRRL 5758

Morphology

Sporulating aerial hyphae consist of hooks, loops and open spirals. Also observed was morphology representative of the rectus flexibilis type. Spores are short and cylindrical and are in chains of 10–50 spores. The spores measure 1.3 $\mu$ × 1.75 $\mu$ with a range of 1.3 $\mu$ to 1.95 × 1.3 $\mu$. The spore surface, as observed by electron microscopy, is smooth.

| Cultural Characteristics of NRRL 5758 on Various Media | |
|---|---|
| Medium | Characteristics |
| ISP No. 2 (yeast extract-malt extract) | Growth-abundant; reverse moderate yellow [11K3]; fair-to-good aerial mycelium and sporulation; white (w) 13 ba and dark grey (Gy) 3 ih; no soluble pigment. |
| ISP No. 3 (oatmeal) | Growth-good; reverse grayish yellow [11B2]; fair aerial mycelium (Gy) dark gray, 3 ih; slight brown soluble pigment. |
| ISP No. 4 (inorganic salts-starch agar) | Growth-abundant; reverse light yellow brown [12E5]; aerial mycelium and spore (W) purplish white 13 ba to (Gy) light gray d; no soluble pigment. |
| ISP No. 5 (glycerol-asparagine agar) | Growth-good; reverse pale yellow-green [10B1]; good aerial mycelium and spores (Gy) yellowish gray 2 dc, to light grayish reddish brown 5 fe; no soluble pigment. |
| Tomato paste-oatmeal agar | Growth-abundant; reverse light yellow brown [13H7]; fair to good aerial mycelium and spores (W) white a to (Gy) medium gray g; very slight brown soluble pigment. |
| Glycerol-glycine agar | Growth-abundant; reverse dark grayish yellow [12I6]; good aerial mycelium and spores (Y) pale yellow 2 db; no soluble pigment. |
| Glucose-asparagin agar | Growth-abundant; reverse grayish greenish yellow [12E2]; abundant aerial mycelium and spores (Gy) yellowish gray 2 dc; very slight brown soluble pigment. |
| Nutrient agar | Growth-good; reverse grayish yellow [12B2]; aerial mycelium and spores, no color assignment because of poor growth; no soluble pigment. |
| Bennett's agar | Growth-abundant, reverse |

Cultural Characteristics of NRRL 5758 on Various Media

| Medium | Characteristics |
| --- | --- |
| Calcium malate agar | grayish yellow [12K3]; scant aerial mycelium and spores (Gy) yellowish gray 2 dc; no soluble pigment. Growth-good; reverse grayish brown [15C8]; no aerial mycelium or sporulation; brown soluble pigment. Area by inoculum cleared. |
| Czapek's solution agar | Growth-poor; no color assignment due to poor growth |
| Emerson's agar | Growth-abundant; reverse grayish yellow [11J5]; no aerial mycelium or spores; no soluble pigment. |
| Tyrosine agar | Growth-abundant; reverse light olive brown [14C4]; abundant aerial mycelium and spores from (W) b (center) to (Gy) light brownish gray 3 fe (margin); very slight broken soluble pigment. |
| Tryptone-yeast agar | Growth-scant; no color assignment. |

The NRRL 5758 organism was studied for selected physiological properties in accordance with standard procedures. The properties observed and characteristics found were as follows:

| Property Observed | Characteristic |
| --- | --- |
| Action on milk | Milk peptonized, white growth ring; cleared area tannish yellow-pH reaction 5.7 |
| Nitrate reduction | Positive |
| Nutrient gelatin | 30% liquefaction at 14 days |
| Melanin pigment production on: | |
| Tyrosine-agar slants | Very weak positive (pigment after 4 days) |
| Difco peptone yeast extract Iron agar slants | Negative |
| Tryptone-yeast-extract broth | Negative |
| Temperature requirements (ISP medium No. 2 yeast extract malt extract slants) | 26–30° C-good growth; 30–37° C.-excellent growth and sporulation; 45° C. slight vegetative growth; reddish soluble pigment. |

The results of carbon utilization tests carried out with organism NRRL 5758 are set forth below. The symbols used to indicate growth response are:
 + good growth, positive utilization
 (+) poor to fair growth
 (−) faint growth, probably no utilization
 − no growth, no utilization

| Carbon Source | Response |
| --- | --- |
| D-glucose | + |
| L-arabinose | + |
| D-xylose | + |
| D-fructose | + |
| sucrose | − |
| D-mannitol | − |
| i-inositol | + |
| rhamnose | + |
| raffinose | − |
| -C control (no carbohydrate) | − |

A second new A-28086-producing organism was derived from *S. aureofaciens* NRRL 5758 by a series of natural selections, followed by chemical mutation. This organism, identified as NRRL 8092, is also classified as a strain of *Streptomyces aureofaciens* Duggar. This classification was based on studies of organism NRRL 8092 using the earlier-described *Streptomyces* classification methods and similar growth conditions. The characteristics of organism NRRL 8092 observed in these studies are summarized in the following paragraphs.

CHARACTERIZATION OF A-28086-PRODUCING STRAIN NRRL 8092

Morphology

On medium ISP no. 7 (tyrosine agar) the culture produces occasional hooks, but mainly produces short, straight sporophores. Spore chains are less than 10 spores per chain, usually 4–7 spores per chain. Short straight spore chains were observed in the following media: ISP no. 3, Czapek's-solution agar and ISP no. 5. Abundant coremia were observed on Emerson's agar. Electron microscope observations were made on tyrosine agar (ISP no. 7) and glucose-asparagine agar. Spores are smooth and range in size from 1.2 to 2.0 $\mu$ in length and about 1.0 $\mu$ in diameter. The average spore size is 1.6 $\mu \times$ 1.0 $\mu$.

Cultural Characteristics of NRRL 8092 on Various Media

| Medium | Characteristics |
| --- | --- |
| ISP No. 2 (yeast extract-malt extract) | Growth-fair; reverse light yellow brown [12H8];fiar aerial mycelium, poor sporulation; aerial pale gray [11A1]; no soluble pigment. |
| ISP No. 3 (oatmeal) | Growth-sparse; reverse hyaline; no aerial mycelium; no soluble pigment. |
| ISP No. 4 (inorganic salts-starch agar) | Growth-moderate; reverse grayish yellow [11B2]; scant aerial mycelium and sporulation; aerial pale yellow gray [10A1]; no soluble pigment. |
| ISP No. 5 (glycerol-asparagine agar) | Growth-moderate; reverse pale yellow [10F2]; fair aerial mycelium; scant sporulation; aerial white [10A1]; no soluble pigment. |
| Tomato paste-oatmeal agar | Growth-moderate; reverse grayish green-yellow; aerial mycelium fair; moderate sporulation, light pale gray [53A2]; no soluble pigment. |
| Glycerol-glycine agar | Growth-abundant; reverse grayish yellow [11E4]; moderate aerial mycelium, white [10A1]; no sporulation; no soluble pigment. |
| Glucose-asparagine agar | Growth-moderate; reverse pale yellow [10F2]; moderate aerial mycelium and sporulation, white [10A1]; no soluble pigment. |
| Nutrient agar | Growth-sparse; reverse pale yellow [10B2]; no aerial mycelium; no soluble pigment. |
| Bennett's agar | Growth-fair; reverse medium yellow pink [11A7]; very scant aerial mycelium; no sporulation; no soluble pigment. |
| Calcium malate agar | Growth-very scant, hyaline; no aerial mycelium; no soluble pigment. |
| Czapek's solution agar | Growth-very scant; reverse hyaline; no aerial mycelium; no soluble pigment. |
| Emerson's agar | Growth-moderate; reverse grayish yellow [11I5]; spotty |

-continued

Cultural Characteristics of NRRL 8092 on Various Media

| Medium | Characteristics |
| --- | --- |
| Tyrosine agar | aerial mycelium; no sporulation; no soluble pigment. Growth-moderate; reverse light yellow brown [12H6]; moderate aerial mycelium, light pale gray margin [53A2], center near white, and moderate sporulation; no soluble pigment. |
| Tryptone-yeast agar | Growth-very scant, hyaline; no aerial mycelium; no soluble pigment. |

Organism NRRL 8092 was also studied for selected physiological properties in accordance with standard procedures. The properties observed and characteristics found were as follows:

| Property Observed | Characteristic |
| --- | --- |
| Action on milk | peptonized (90%); pale-yellow growth ring, cleared area pale yellow--pH reaction 4.6 |
| Nitrate reduction | Positive |
| Nutrient gelatin | 50% hydrolyzed at 14 days |
| Melanin pigment production on: | |
| Tyrosine-agar slants | Very weakly positive |
| Tryptone-yeast-extract broth | Negative |
| Carrot plug | Abundant growth, pale yellow; no aerial mycelium |
| Potato plug | Abundant growth, grayish white; no aerial mycelium; no change in plug. |
| Temperature requirements (ISP medium No. 2 yeast extract malt extract slants) | 25° C.-Abundant growth; fair aerial mycelium; reverse light brown; no soluble pigment. 30° C.-Abundant growth; fair aerial mycelium; reverse light brown; no soluble pigment. 37° C.-Abundant growth; fair aerial mycelium; reverse-brown; soluble pigment brown. 40° C.-Abundant growth; sparse aerial mycelium; reverse red brown; soluble pigment deep red brown. 45° C.-Fair growth; no aerial mycelium; reverse red brown; moderate red brown pigment. |

The results of carbon utilization tests carried out with organism NRRL 8092 are set forth below. The symbols used to indicate growth response are:

+ good growth, positive utilization
(+) poor to fair growth
(−) faint growth, probably no utilization
− no growth, no utilization

| Carbon Source | Response |
| --- | --- |
| D-glucose | + |
| L-arabinose | + |
| D-xylose | + |
| D-fructose | + |
| sucrose | − |
| D-mannitol | − |
| i-inositol | + |
| rhamnose | + |
| raffinose | − |
| -C control (no carbohydrate) | − |

Certain characteristics of the A-28086-producing *S. aureofaciens* strains differ from the characteristics of the organism described by Shirling and Gottlieb. These differences are summarized in Table III:

TABLE III

| Carbon utilization | NRRL 5758 | NRRL 8092 | Published Description |
| --- | --- | --- | --- |
| sucrose | − | − | + |
| i-inositol | + | + | − |
| rhamnose | + | + | |
| Gelatin Liquification | 30% in 14 days | 50% in 14 days | Limited or None |
| Action on Milk | Milk peptonized, white growth ring | Milk peptonized, pale-yellow growth ring | Limited and variable peptonization (often none); limited growth and coagulation |

The characteristics of organism NRRL 5758 which differ from the characteristics of organism NRRL 8092 are summarized in Table IV.

Table IV

| Characteristic | NRRL 5758 | NRRL 8092 |
| --- | --- | --- |
| Vegetative Color | Yellow on several media | Cream to pale-yellow on several media |
| Sporulation | Some spiral sporophores on tomato-paste:oatmeal and inorganic salts-starch media | Short straight sporophores with occasional hooks |
| Growth on: | | |
| Calcium malate | Growth fair, brown; with clearing | Growth sparse, clear, no clearing |
| Inorganic salts-starch | Moderate sporulation; aerial purplish white to gray. | Scant sporulation; aerial pale yellow gray |
| Bennett's agar | Reverse pale-yellow | Reverse pink |

The *Streptomyces aureofaciens* cultures useful for production of A-28086 antibiotics have been deposited and made a part of the stock culture collection of the Northern Marketing and Nutrition Research Division, U.S. Dept. of Agriculture, Agricultural Research Service, Peoria, Ill., 61604, from which they are available to the public under the numbers NRRL 5758 and NRRL 8092.

The culture medium employed to grow *Streptomyces aureofaciens* NRRL 5758 or *Streptomyces aureofaciens* NRRL 8092 can be any one of a number of media. For economy in production, optimal yield, and ease of product isolation, however, certain culture media are preferred. Thus, for example, preferred carbohydrate sources in large-scale fermentation are tapioca dextrin and sucrose, although glucose, corn starch, fructose, mannose, maltose, lactose, and the like can also be employed Corn oil, peanut oil, soybean oil and fish oil are other useful sources of carbon. A preferred nitrogen source is enzyme-hydrolyzed casein, although peptones, soybean meal, cotton-seed meal, amino acids such as glutamic acid, and the like are also useful. Among the nutrient inorganic salts which can be incorporated in the culture media are the customary soluble salts capable of yielding sodium, magnesium, calcium, ammonium, chloride, carbonate, sulfate, nitrate, and like ions.

Essential trace elements necessary for the growth and development of the organism should also be included in the culture medium. Such trace elements commonly occur as impurities in other constituents of the medium in amounts sufficient to meet the growth requirements of the organism.

It may be necessary to add small amounts (i.e. 0.2 ml/l.) of an antifoam agent such as polypropylene glycol to large-scale fermentation media if foaming becomes a problem.

Although it is not essential, the antibiotic production of the A-28086-producing *Streptomyces aureofaciens* strains is enhanced by the addition of a small amount of oil such as soybean oil.

For production of substantial quantities of the A-28086 antibiotics, submerged aerobic fermentation in tanks is preferred. Small quantities of the A-28086 antibiotics may be obtained by shake-flask culture. Because of the time lag in antibiotic production commonly associated with innoculation of large tanks with the spore form of the organism, it is preferable to use a vegetative inoculum. The vegetative inoculum is prepared by inoculating a small volume of culture medium with the spore form or mycelial fragments of the organism to obtain a fresh, actively growing culture of the organims. The vegetative inoculum is then transferred to a larger tank. The medium used for the growth of the vegetative inoculum can be the same as that employed for larger fermentations, but other media can also be employed.

The A-28086-producing organisms can be grown at temperatures between about 20° and about 40° C. Optimum A-28086 production appears to occur at temperatures of about 27°–30° C.

As is customary in aerobic submerged culture processes, sterile air is blown through the culture medium. For efficient growth of the organism the volume of air employed in the tank production is preferably above 0.1 volume of air per volume of culture medium per minute. For efficient production of the A-28086 antibiotics the volume of air employed in the tank production is preferably above 0.25 volume of air per volume of culture medium per minute. High levels of dissolved oxygen do not depress antibiotic production.

The production of antibiotics can be followed during the fermentation by testing samples of the broth or of extracts of the mycelial solids for antibiotic activity against organisms known to be sensitive to the antibiotics. One assay organism useful in testing the antibiotics of the present inventin is *Bacillus subtilis* ATCC 6633. The bioassay is conveniently performed by paper-disc assay on agar plates.

The initial pH of the uninoculated culture medium varies with the medium used. In general, the pH should be in the range of 6.0 to 7.5. The harvest pH at the end of the fermentation is usually slightly higher, in the range of 6.5 to 8.0.

Generally, antibiotic activity is detectable on the second day of the fermentation. Maximum production of antibiotic activity usually occurs between about the sixth and the tenth days.

Following their production under submerged aerobic fermentation conditions, the A-28086 antibiotics previously described can be recovered from the fermentation medium by methods commonly employed in the fermentation art. The antibiotic activity produced during fermentation of an A-28086-producing organism occurs in both the mycelial mass and in the filtered broth. Maximum recovery of the A-28086 antibiotics is accomplished, therefore, by a combination of methods, including filtration, extraction, and adsorption chromatography. A preferred solvent for separating the A-28086 antibiotics from either whole or filtered fermentation broth is ethyl acetate, although other commonly used solvents are satisfactory.

An especially advantageous method of separating the A-28086 factors A, B and D is to lower the pH of the whole fermentation broth to about pH 3.0. At this pH 3.0 the A-28086 factors A, B, and D are conveniently separated with the mycelial mass by filtration. This method is the subject of a copending application of Boeck and Berg titled ANTIBIOTIC RECOVERY PROCESS, Ser. No. 569,712, filed this even date herewith. Another advantageous method of separating the A-28086 factors involves adding a bicarbonate such as, for example, sodium bicarbonate, to the whole broth in amounts of approximately one gram per liter. The A-28086 factors are, thereby, conveniently separated with the mycelial mass in salt form. Methanol is a preferred solvent for separating the antibiotics from the mycelial mass, but other lower alcohols and ketones are also suitable.

Azeotropic distillation can also be advantageously employed in the recovery of the A-28086 antibiotics. In this method an organic solvent which forms an appropriate azeotrope with water is added to the aqueous fermentation broth. This solvent-broth mixture is subjected to azeotropic distillation in order to remove at least half the water from the broth, leaving a water-solvent mixture in which the A-28086 antibiotics are in solution in the organic solvent. Insoluble by-products can be separated by suitable means such as filtration or centrifugation. The A-28086 antibiotics can then be recovered from the organic solution by well-known procedures such as evaporation of solvent, precipitation by adding a nonsolvent, or extraction.

Organic solvents which form appropriate azeotropes with water in order to carry out such a recovery procedure include, illustratively, butyl alcohol, amyl alcohol, hexyl alcohol, benzyl alcohol, butyl acetate, amyl acetate, 1,2-dichloroethane, 3-pentanone, 2-hexanone, benzene, cyclohexanone, toluene, the xylenes and the like.

There is special advantage in recovery by azeotropic distillation on large-scale fermentation processes. Both water and solvent taken overhead in the azeotrope can be separated by known techniques and thereafter recycled for further use. The water thus removed is free of contaminants and does not require a waste disposal process. The solvent thus removed may be recycled to the process.

Further purification of the A-28086 antibiotics includes additional extraction and adsorption procedures. Adsorptive materials such as silica gel, carbon, Florisil (magnesium silicate, Floridin Co., P.O. Box 989, Tallahassee, Fla.) and the like can be advantageously employed.

Alternatively, the culture solids, including medium constituents and mycelium can be used without extraction or separation, but preferably after removal of water, as a source of the A-28086 antibiotics. For example, after production of A-28086 antibiotic activity, the culture medium can be dried by lyophilization and mixed directly into feed premix.

In another aspect, after production of A-28086 activity in the culture medium, the mycelium can be separated and dried to give a product which can be used directly in a feed premix. When separating the mycelium for such use, the addition of calcium carbonate (about 10 g./l.) aids in filtration and gives an improved dried product.

Under the conditions employed thus far, the Streptomyces aureofacens strains described previously and designated as NRRL 5758 and NRRL 8092 produce antibiotic A-28086 factor A as the predominant factor. Although the ratio of factors varies depending on the fermentation conditions used, in general factor A accounts for more than 99 percent of the total recovered antibiotic activity from NRRL 5758 and for about 90 percent of the total recovered antibiotic activity from NRRL 8092. A-28086 factor B accounts for most of the remaining antibiotic activity from NRRL 5758, and factor D is a minor factor. On the other hand, A-28086 factor D accounts for about 8–10 percent of the total recovered antibiotic activity from NRRL 8092, and factor B is a minor factor.

Antibiotic A-28086 factors A, B, and D are separated from each other and are isolated as individual compounds by the use of well-known methods such as column chromatography, thin-layer chromatography and the like. For example, column chromatography over silica gel is used to separate factors A, B, and D by eluting the column with varying solvent mixtures, such as benzene-ethyl acetate. Using benzene-ethyl acetate solvent mixtures over a silica gel column, factor B is eluted first, and factors A and D are eluted later. Thin-layer chromatography, as described hereinabove, is a convenient method for monitoring elution progress.

The A-28086 compounds of this invention inhibit the growth of bacteria and fungi which are pathogenic to animal and plant life. The relative microbiological activities of A-28086 factors A and B are described below in Table V.

The test method was the conventional disc-diffusion method (6 mm pads were dipped in solutions containing 1 mg of compound/ml of solution; pads were placed on agar plates seeded with test organism).

TABLE V

| Test Organism | Zone of Inhibition (mm) | |
|---|---|---|
| | A28086 factor A | A28086 factor B |
| Staphylococcus aureus | 19 | 21 |
| Bacillus subtilis ATCC6633 | 28 | 31 |
| Sarcina lutea ATCC9341 | 26 | 16 |
| Mycobacterium avium ATCC7992 | 12 | 12 |
| Saccharomyces pastorianum ATCC2366 | 17 | — |
| Candida tropicalis | 14 | 14 |
| Fusarium moniliforme | 12 | Not Tested |

In one important aspect, the A-28086 compounds inhibit the growth of anaerobic bacteria. The minimal inhibitory concentrations (MIC) at which A-28086 factor A inhibits various anaerobic bacteria, determined by standard agar-dilution assay, are summarized in Table VI. Endpoints were read after 24-hour incubation.

TABLE VI

| Test Organism | MIC ($\mu$g/ml) |
|---|---|
| Actinomyces bovis | <0.5 |
| Clostridium inocuum | <0.5 |
| Clostridium perfringens | <0.5 |
| Clostridium ramosum | 4.0 |

TABLE VI-continued

| Test Organism | MIC ($\mu$g/ml) |
|---|---|
| Clostridium septicum | <0.5 |
| Clostridium septicum bovine | <0.5 |
| Eubacterium aerofaciens | 1.0 |
| Peptococcus anaerobius | <0.5 |
| Peptostreptococcus intermedius | 16.0 |
| Propionibacterium acnes 44 | 16.0 |
| Propionibacterium acnes 79 | 2.0 |
| Bacteroides fragilis ssp. fragilis | 8.0 |
| Bacteroides fragilis ssp. thetaiotacmicron | 8.0 |
| Bacteroides fragilis ssp. vulgatis No. 1563 | 8.0 |
| Bacteroides fragilis ssp. vulgatis 1211 | 2.0 |
| Fusobacterium symbiosum | <0.5 |
| Fusobacterium necrophorum | 8.0 |
| Veillonella alcalescens | 16.0 |

The $C_2$–$C_6$-acyl ester derivatives of A-28086 factor A also have antibacterial and antifungal activity. In one aspect, these derivatives have increased gram-positive activity. The relative gram-positive activities of certain of these derivatives were compared with the activity of factor A. The compounds were tested by turbidometric, assay on a semiautomated system (Autoturb microbiological assay system, Elanco) described by N. R. Kuzel and F. W. Kavanaugh in J. Pharmaceut. Sci. 60 (5), 764 and 767 (1971). In testing the A-28086 antibiotics, the following test parameters were used: Staphylococcus aureus (H-Heatley) NRRL B-314 in a nutrient broth medium (pH 7), incubated for 4 hours at 37° C. Test samples and the standard were dissolved in methanol-water (10:90). The standard, A-28086 factor A, was presented to the Autoturb carrousel at concentrations of 2, 3, 4, and 5 mcg/ml. Test compounds were diluted to contain approximately 3 or 4 mcg of activity per ml, as presented to the carrousel. The relative activities of test compounds, as compared to that of the standard, are given below:

| Compound | Relative G$^+$ Activity |
|---|---|
| A28086 factor A (standard) | 1 |
| A28086-A acetyl ester derivative | 2.5 |
| A28086-A propionyl ester derivative | 7 |
| A28086-A n-butyryl ester derivative | 8 |
| A28086-A n-valeryl ester derivative | 14 |
| A28086-A n-caproyl ester derivative | 20 |

Activity against Mycoplasma is another useful aspect of the antimicrobial activity of the A-28086 compounds. Mycoplasma species, also known as pleuropneumonia-like (PPLO) organisms, are pathogenic to man and various animals. Agents active against PPLO organisms are especially needed by the poultry industry. The minimal inhibitory concentrations (MIC) of antibiotic A-28086 factor A against various Mycoplasma species, as determined by in vitro broth-dilution studies, are summarized in Table VII below:

TABLE VII

| Organism | MIC(mcg/ml) |
|---|---|
| M. gallisepticum | 12.5 |
| M. hyorhinis | 12.5 |
| M. synoviae | 6.25 |

TABLE VII-continued

| Organism | MIC(mcg/ml) |
| --- | --- |
| M. hypopneumoniae | 6.25 |
| M. hyosynoviae | 6.25 |

In one embodiment, therefore, this invention provides an anti-PPLO agent. Solutions containing as little as 10 micrograms of antibiotic A-28086 per milliliter of solution are useful for disinfecting surfaces to protect animals from various Mycoplasma species.

The A-28086 compounds also are antiviral agents. A-28086 factor A is active against type III poliovirus, vacinia virus, herpes virus and Semliki Forest virus, as demonstrated by in vitro plaque suppression tests, similar to that described by Siminoff, *Applied Microbiology* 9 [1], 66–72 (1961). A-28086 factor A is also active against Transmissible Gastro-enteritis virus, Newcastle Disease virus, and Infectious Bovine Rhinotracheitis virus, as demonstrated by similar tissue-culture tests.

In one aspect of this invention, therefore, an A-28086 compound can be administered orally, topically or parenterally to mammals for the control of viruses. Useful dosage levels for prevention or treatment of viral disease vary from about 1 to about 5 mg/kg of mammalian body weight, depending upon the virus and upon whether the drug is to be used prophylactically or therapeutically.

Furthermore, solutions containing an A-28086 compound, preferably together with a surfactant, can be used to decontaminate the in vitro habitat on which viruses, such as polio or herpes, are present. Solutions containing from about 1 to about 1500 mcg/ml of an A-28086 compound are effective in the control of viruses.

The acute toxicity of antibiotic A-28086 factor A, administered intraperitoneally to mice and expressed as $LD_{50}$, is 7.15 mg/kg.

The A-28086 compounds of this invention are also insecticides and acaricides. The A-28086 compounds are active against insects such as Mexican bean beetle, milkweed bug, and house fly and against mites such as two-spotted spider mite when applied at rates as low as 500 ppm. In addition, the A-28086 compounds are active against mosquito larvae when applied at rates as low as one ppm.

Anticoccidial activity is an important property of the A-28086 compounds of this invention. For example, feeding experiments show that an A-28086 compound, when present in the feed of young chickens at levels as low as 0.003 percent, improves weight gains and, at levels as low as 0.005 percent, prevents mortality and decreases the number of lesions in chicks which have been challenged with coccidia. The results of tests with factor A in chicks challenged with various Fimeria species are shown in Tables VIII through X.

TABLE VIII

ACTIVITY OF ANTIBIOTIC A-28086 FACTOR A AGAINST *EIMERIA TENELLA*.

| Drug Level in Feed, Percent by Weight | No. Of Chickens | Percent Mortality | Percent Weight Gain | Average Lesion Score | Percent Reduction in Lesion Score |
| --- | --- | --- | --- | --- | --- |
| 0.04 | 10 | 0 | 50 | 0 | 100 |
| 0.02 | 10 | 0 | 82 | 0.2 | 95 |
| 0.01 | 10 | 0 | 94 | 0.2 | 95 |
| Infected Controls | 20 | 35 | 68 | 3.65 | — |
| Normal Controls | 20 | 0 | 100 | — | — |
| 0.02 | 20 | 0 | 84 | 0 | 100 |
| 0.01 | 20 | 0 | 96 | 0 | 100 |
| 0.005 | 20 | 0 | 91 | 2.8 | 27 |
| 0.0025 | 20 | 10 | 87 | 3.85 | 0 |
| Infected Controls | 20 | 40 | 74 | 3.85 | — |
| Normal Controls | 20 | 0 | 100 | — | — |

TABLE IX

ACTIVITY OF ANTIBIOTIC A-28086 FACTOR A AGAINST VARIOUS *EIMERIA* SPECIES[1]

| Infecting Organism | Drug Level in Feed, Percent by Weight | Percent Mortality | Percent Weight Gain | Average Lesion Score | Percent Reduction in Lesion Score | Oocysts Passed Total/Bird ($1 \times 10^6$) | Percent Reduction |
| --- | --- | --- | --- | --- | --- | --- | --- |
| Eimeria acervulina | 0.005 | 0 | 87 | 0.75 | 53 | 6.15 | 83 |
|  | 0.0025 | 0 | 82 | 1.25 | — | 4.91 | 86 |
| Infected Controls | — | 0 | 63 | 1.60 | — | 36.32 | — |
| Eimeria maxima | 0.005 | 0 | 85 | 0.2 | 85 | 1.95 | 40 |
| Infected Controls |  | 0 | 65 | 1.3 | — | 3.24 | — |
| Eimeria brunetti | 0.005 | 0 | 88 | 1.2 | — | 2.31 | 58 |
| Infected Controls | — | 0 | 62 | 1.7 | — | 5.55 | — |

[1]Four replicates, 5 broiler cockerels each

TABLE X

ACTIVITY OF ANTIBIOTIC A-28086 FACTOR A AGAINST MIXED *EIMERIA* SPECIES

| Infecting Organism | Drug Level In Percent by Weight | Percent Mortality | Percent Weight Gain | Intestinal Lesions | | Cecal Lesions | |
| --- | --- | --- | --- | --- | --- | --- | --- |
|  |  |  |  | Average | Percent Reduction | Average | Percent Reduction |
| E. necatrix and |  |  |  |  |  |  |  |

TABLE X-continued
ACTIVITY OF ANTIBIOTIC A-28086 FACTOR A AGAINST MIXED *EIMERIA* SPECIES

| Infecting Organism | Drug Level In Percent by Weight | Percent Mortality | Percent Weight Gain | Intestinal Lesions Average | Intestinal Lesions Percent Reduction | Cecal Lesions Average | Cecal Lesions Percent Reduction |
|---|---|---|---|---|---|---|---|
| E. tenella | 0.005 | 0 | 94 | 0.7 | 59 | 1.75 | 50 |
| Infected Controls | | 20 | 52 | 1.7 | — | 3.5 | — |
| E. tenella, E. necatrix, E. maxima, E. brunetti, E. acervulina, and E. mivati | 0.01 | 0 | 91 | 0.4 | 79 | 0.9 | 73 |
| Infected Controls | — | 50 | 12 | 1.9 | — | 3.3 | — |

¹Four replicates, 5 broiler cockerels each.

For the prevention or treatment of coccidiosis in poultry, a non-toxic anticoccidial amount of an A-28086 compound is administered to birds, preferably orally on a daily basis. The A-28086 compound can be supplied in many ways, but it is most conveniently supplied with a physiologically-acceptable carrier, preferably the feed ingested by the birds. Although a variety of factors must be considered in determining an appropriate concentration of A-28086 compound, the rates of administration will be generally in the range of 0.003 to 0.04 percent by weight of unmedicated feed, and preferably in the range of 0.005 to 0.02 percent.

The ability to improve feed-utilization efficiency in animals is another important property of A-28086 compounds. For example, A-28086 compounds improve feed-utilization efficiency in ruminants which have a developed rumen function.

As discussed hereinabove, efficiency of carbohydrate utilization in ruminants is increased by treatments which stimulate the animal's rumen flora to produce propionate compounds rather than acetate or butyrate compounds. The efficiency of feed use can be monitored by observing the production and concentration of propionate compounds in the rumen, using the following methods:

Rumen fluid is obtained from a steer with a surgically-installed fistula opening into the rumen. The steer is maintained on a high-grain ration. A sample of rumen fluid is strained through four layers of cheesecloth, and the filtrate is collected. The particulate matter retained by the cheesecloth is resuspended in enough physiological buffer to return it to the original volume of the rumen fluid, and this suspension is strained again. The buffer used has the following composition:

| Ingredient | g/liter |
|---|---|
| Na₂HPO₄ | 0.316 |
| KH₂PO₄ | 0.152 |
| NaHCO₃ | 2.260 |
| KCl | 0.375 |
| NaCl | 0.375 |
| MgSO₄ | 0.112 |
| CaCl₂ . 2H₂O | 0.050 |
| FeSO₄ . 7H₂O | 0.008 |
| MnSO₄ . H₂O | 0.004 |
| ZnSO₄ . 7H₂O | 0.004 |
| CuSO₄ . 5H₂O | 0.002 |
| CoCl₂ . 6H₂O | 0.001 | as described by Cheng et al. in *J. Dairy Sci.* 38, 1225–1230 (1955).

The two filtrates are combined and allowed to stand until particulate matter separates to the top. The clear layer is separated, diluted with the same buffer (1:1) and then adjusted to between pH 6.8 to 7.0.

The diluted rumen fluid (10 ml) is placed in a 25-ml flask with 40 mg of the above-described feed, an additional 1 mg of soybean protein, and the compound to be tested. Four replicate flasks are used per treatment. Two sets of four control flasks each are also employed. A zero-time control and an incubated 16-hour control are used. All test flasks are incubated for 16 hours at 38° C. After incubation the pH is measured, and 25 percent metaphosphoric acid (2 ml) is added to each flask. The samples are allowed to settle, and the supernatants are analyzed by gas chromatography for propionate, acetate, and butyrate compounds. Active compounds significantly increase propionate production over that of controls.

Test-compound results are statistically compared with control results. Table XI shows the ratio of volatile-fatty-acid concentrations in treated flasks to concentrations in control flasks.

TABLE XI

| Compound | ppm in rumen fluid | Ratio of Treated to Control Molar % acetate | Ratio of Treated to Control Molar % butyrate | Ratio of Treated to Control Molar % propionate | Total VFA mM/l |
|---|---|---|---|---|---|
| A-28086 Factor A | 1 | 0.94 | 0.87 | 1.34 | 1.26 |
| A-28086 Factor B | 1 | 0.97 | 0.96 | 1.15 | 1.29 |
| A-28086 Factor A-Acetyl Ester | 1 | 0.79 | 0.76 | 2.04 | 1.04 |
| A-28086 Factor A-Propionyl Ester | 1 | 0.90 | 0.68 | 1.73 | 1.25 |
| A-28086 Factor A Butyryl Ester | 1 | 0.91 | 0.81 | 1.56 | 1.19 |
| A-28086 Factor A-Valeryl Ester | 1 | 0.92 | 0.79 | 1.55 | 1.18 |
| A-28086 Factor A-Caproyl Ester | 1 | 0.86 | 0.97 | 1.57 | 0.99 |

Efficiency of carbohydrate utilization is further demonstrated by in vivo tests performed in animals which have had fistulas installed in their rumens, making it possible to withdraw specimens of the contents of the rumen.

The test reported in Table XII was conducted with mature fistulated steers weighing about 1,000 lbs. each. Two steers were fed a normal diet, and four steers in each treatment group were fed an identical diet to which A-28086 factor A had been added. To each aliquot (100 ml) of rumen fluid taken, 10 percent metaphosphoric acid (100 ml) was added. The samples were allowed to settle, and the supernatants were analyzed by gas chromatographic methods to determine propionic acid concentrations.

The results in Table XII are the mean percent increases in ruminal propionic acid concentration, averaged over five analyses in a 14-day treatment period. Controls had approximately 20 molar percent propionic acid.

TABLE XII

| A-28086 factor (mg/day) | Percent Increase Over Control |
| --- | --- |
| 25 | 17.4 |
| 100 | 54.0 |

Furthermore, in vivo testing demonstrated that A-28086 factor A increases feed-utilization efficiency in sheep. The results of these tests, conducted over a period of 56 days, are summarized in Table XIII.

TABLE XIII

| A-28086-Factor A (g) per ton of feed | Number of Animals | Average Daily Gain (lbs./day) | Feed Intake (lbs./day) | Feed/ Gain | Percent Improvement |
| --- | --- | --- | --- | --- | --- |
| 9 | 13 | .44 | 3.29 | 7.40 | 12 |
| 18 | 13 | .38 | 3.15 | 8.31 | 1 |
| Control | 17 | .42 | 3.56 | 8.38 | — |

Kinashi et al. in *Tetrahedron Lett.* 49, 4955-4958 (1973) reported the antibiotic salinomycin to have the following structure (III)*

This invention relates, therefore, to a method of increasing feed-utilization efficiency in ruminants by administering a propionate-increasing amount of a compound selected from a group consisting of an A-28086 compound as specified, salinomycin, the $C_2$-$C_6$-acyl ester derivatives of salinomycin, and the physiologically-acceptable salts of salinomycin and of said ester derivatives. The physiologically-acceptable salts of salinomycin and of its $C_2$-$C_6$-acyl ester derivatives are those salts as specified for A-28086 factor A and its $C_2$-$C_6$-acyl ester derivatives and are prepared in a similar manner. The $C_2$-$C_6$-acyl ester derivatives of salinomycin are prepared by the same method used to prepare the $C_2$-$C_6$-acyl ester derivatives of A-28086 factor A.

The compounds of this invention are typically effective in increasing propionates and, thereby, the efficiency of feed-utilization when administered to ruminants orally at rates of from about 0.05 mg/kg/day to about 5.0 mg/kg/day. Most beneficial results are achieved at rates of from about 0.1 mg/kg/day to about 2.5 mg/kg/day. A preferred method of administration of a compound of this invention is by mixing it with the animals'feed; however, it can be administered in other ways, for example, tablets, drenches, boluses, or capsules. Formulation of these various dosage forms can be accomplished by methods well known in the veterinary pharmaceutical art. Each individual dosage unit should contain a quantity of a compound of this invention directly related to the proper daily dose for the animal to be treated.

This invention further relates to feed compositions

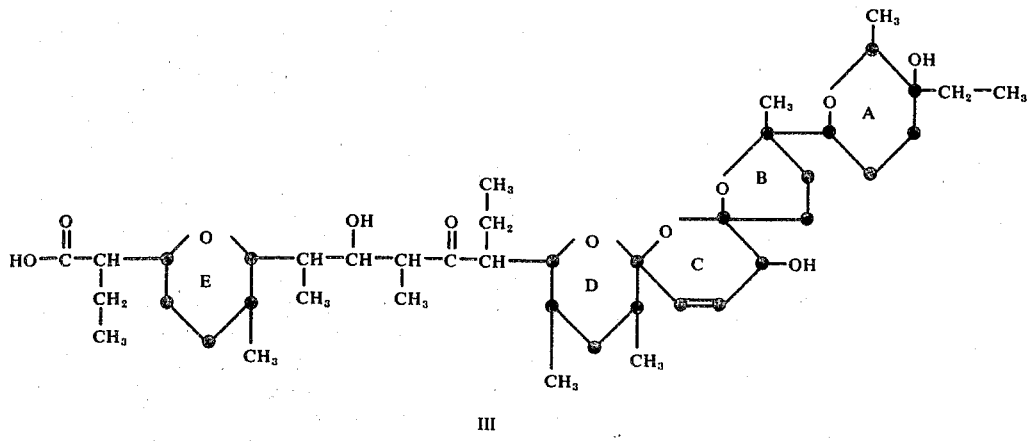

III

As will be apparent upon comparison of salinomycin's structure with that proposed for antibiotic A-28086 factor A, the structures are quite similar. A-28086 factor A differs only in that it has an additional methyl group on the E ring. A-28086 factors A, B, and D are, however, distinctly different from a comparison sample of salinomycin on various paper and thin layer chromatographic systems.

adapted to fatten cattle comprising cattle feed and from 1 to 30 grams per ton of a compound selected from a group consisting of an A-28086 compound as specified, salinomycin, the $C_2$-$C_6$-acyl ester derivatives of salinomycin, and the physiologically-acceptable salts of salinomycin and of said ester derivatives.

As is recognized by those skilled in the art, cattle feeds are different from other feeds, such as poultry feeds. Cattle rations contain roughages such as, for example, cottonseed hulls and corn silage. In addition, cattle feeds contain a high percentage, often from 15–25 percent, of non-protein nitrogen sources. A common non-protein nitrogen source is urea.

As described above, the A-28086 compounds are antiviral agents and are also active against anaerobic bacteria, particularly *Clostridium perfringens*. The A-28086 compounds are, therefore, beneficial in the treatment or prevention of enteritis in chickens, swine, cattle and sheep. The A-28086 compounds are also useful in the treatment of enterotoxemia in ruminants.

In order to illustrate more fully the operation of this invention the following examples are provided.

EXAMPLE 1

A. Shake-flask Fermentation of A-28086 using S. aureofaciens NRRL 5758

A culture of *Streptomyces aureofaciens* NRRL 5758 was prepared and maintained on an agar slant having the following composition:

| Ingredient | Amount |
| --- | --- |
| Agar | 20 g |
| Dextrin | 10 g |
| Enzyme-hydrolyzed casein | 2 g |
| Beef extract | 2 g |
| Yeast extract | 2 g |
| Distilled water | q.s. 1 liter |

The slant was inoculated with *Streptomyces aureofaciens* NRRL 5758, and the inoculated slant was incubated at 30° C. for 6 to 10 days. The mature slant culture was covered with beef serum, and scraped with a sterile loop to loosen the spores. The resulting beef-serum suspension of spores and mycelial fragments was lyophilized into six pellets.

One lyophilized pellet thus prepared was used to inoculate 50 ml of a vegetative medium having the following composition:

| Ingredient | Amount |
| --- | --- |
| Glucose | 20 g |
| Soybean grits | 15 g |
| Corn-steep liquor | 10 g |
| CaCO$_3$ | 2 g |
| Tap Water | q.s. 1 liter |
| The inoculated vegetative medium, in a 250-ml | |

The inoculated vegetative medium, in a 250-ml Erlenmeyer flask, was incubated at 30° C. for 72 hours on a shaker rotating through an arc 2 inches in diameter at 250 rpm.

B. Tank Fermentation of A-28086 using *S. aureofaciens* NRRL 5758

In order to provide a larger volume of inoculum, 10 ml of the incubated vegetative medium described above was used to inoculate 400 ml of a second-stage vegetative growth medium having the same composition as that of the vegetative medium. This second-stage medium, in a 2-liter flask, was incubated at 30° C. for 24 hours on a shaker rotating through an arc 2 inches in diameter at 250 rpm.

This second-stage vegetative medium (1 l.) was used to inoculate 100 liters of sterile production medium of the following composition:

| Ingredient | Amount |
| --- | --- |
| Tapioca dextrin | 60.0 g/l. |
| Enzyme-hydrolyzed casein | 8.0 g/l. |
| Molasses | 15.0 g/l. |
| MgSO$_4$ . 7H$_2$O | 0.5 g/l. |
| CaCO$_3$ | 2.0 g/l. |
| Refined soybean oil | 5.0 g/l. |
| Deionized water | q.s. 1 liter |

The pH of the medium was 6.7 after sterilization by autoclaving at 120° C. for 30 minutes at 15–20 pounds pressure. In a 165-liter fermentation tank, the inoculated production medium was allowed to ferment for 10 days at a temperature of 29° C. The fermentation medium was aerated with sterile air at the rate of 0.4 volumes of air per volume of culture medium per minute. The medium was stirred with conventional agitators at 250 rpm.

EXAMPLE 2

The A-28086 antibiotics were produced according to the process of Example 1, but utilizing a flask-production medium having the following composition:

| Ingredient | Amount |
| --- | --- |
| Glucose | 10 g/l. |
| Edible molasses | 20 g/l. |
| Peptone | 5 g/l. |
| CaCO$_3$ | 2 g/l. |
| Tap water | q.s. 1 liter |

EXAMPLE 3

Separation of the A-28086 Antibiotic Complex Produced by S. aureofaciens NRRL 5758

Whole fermentation broth (132.1.), obtained by the method described in Example 1, was filtered with a filter aid (Hyflo Super-cel, a diatomaceous earth, Johns-Manville Products Corp.) to give 97 liters of filtered broth. The filtered broth was extracted with an approximately equal volume of ethyl acetate. The ethyl acetate extract was separated from the aqueous phase and was concentrated to a volume of about 500 ml. This concentrated ethyl acetate extract was added to a large excess of petroleum ether (Skelly Solve F; about 10.1.) to precipitate and, thereby, separate unwanted material. The separated filtrate was evaporated under vacuum to give the broth portion of A-28086 antibiotic complex (6.9 g).

The mycelial portion of A-28086 antibiotic complex was obtained by extracting the filtered mycelium twice with approximately half volumes of methanol (62 1. and 59 1.). The two methanol extracts were combined and were concentrated under vacuum to remove the methanol. After this concentration about 10 1. of an aqueous phase remained. This aqueous phase was adjusted to about pH 7.5 with dilute sodium hydroxide. The resulting solution was extracted twice with approximately equal volumes of ethyl acetate (9 1. and 10 1.). The ethyl acetate extracts were combined and then concentrated to a volume of about 400 ml. This concentrated ethyl acetate extract was added to a large excess of petroleum ether to remove unwanted materials, using the procedure described above for the concentrated filtered broth extract. The mycelial portion of A-28086 antibiotic complex obtained from the filtrate weighed 20.6 g.

EXAMPLE 4

Isolation of A-28086 Individual Factors A and B

The mycelial portion of A-28086 antibiotic complex (235 g, prepared as described in Example 3) was dissolved in about 80 ml of benzene. This benzene solution was applied to a silica gel column (9 × 130cm, 8 l., Matheson grade 62 silica gel). The column was eluted with varying benzene-ethyl acetate mixtures. Elution progress was followed by thin-layer chromatography. Using a benzene-ethyl acetate (90:10) solvent system, factor B was eluted first and was isolated as an individual factor. Factor B (43 mg) was crystallized from acetone-water, m.p. 150°-153° C.

Continuing to elute with benzene-ethyl acetate mixtures but gradually increasing the ratio of ethyl acetate present, factor A was eluted; the various fractions containing factor A were combined and were concentrated under vacuum to a residue. This residue was dissolved in acetone (about 150 ml); water (about 150 ml) was added to the acetone solution. The pH of the resulting solution was adjusted to pH 3 by the addition of 1 N hydrochloric acid. The acidified mixture was stirred about one hour, during which time a precipitate formed. This precipitate was separated by filtration and was recrystallized from acetone (about 150 ml) upon addition of water (about 60 ml). The product was dried overnight under vacuum to give factor A (about 6.6 g). After partial evaporation of acetone from the filtrate, a second crop of factor A (about 1.2 g) was obtained.

EXAMPLE 5

A-28086 Factor A-Acetyl Ester Derivative

Antibiotic A-28086 factor A (7.4 g) was dissolved in pyridine (150 ml). Acetic anhydride (50 ml) was added to this solution. The resulting solution was mixed thoroughly and then was allowed to stand overnight at room temperature.

Water (200 ml) was added, mixing thoroughly. This mixture was allowed to stand for four hours at room temperature. A white solid precipitated; this solid was separated by filtration, washed with water, and air dried. The resulting solid was dissolved in acetone (100 ml); and the acetone solution was evaporated to dryness under vacuum (this was repeated three times). The residue thus obtained crystallized from acetone (100 ml)-water (50 ml), to give A-28086 factor A acetyl ester derivative (6.14 g), melting point 100°-103° C.

EXAMPLES 6-9

Antibiotic A-28086 factor A propionyl ester derivative, prepared by reacting factor A with propionic anhydride in the presence of pyridine according to the method of Example 5, melting point 96°-98° C.

Antibiotic A-28086 factor A n-butyryl ester derivative, prepared by reacting factor A with n-butyric anhydride in the presence of pyridine according to the method of Example 5, melting point 79°-81° C.

Antibiotic A-28086 factor A n-caproyl ester derivative, prepared by reacting factor A with caproic anhydride in the presence of pyridine according to the method of Example 5, melting point 163°-167° C.

Antibiotic A-28086 factor A n-valeryl ester derivative, prepared by reacting factor A with valeric anhydride in the presence of pyridine according to the method of Example 5, melting point 173°-175° C.

EXAMPLE 10

Preparation of A-28086 Factor A Sodium Salt

Antibiotic A-28086 factor A (500 mg) was dissolved in acetone (50 ml). Water (50 ml) was added to this solution, and 5 N sodium hydroxide was added to bring the pH of the solution to 10.5-11. The resulting solution was stirred for one hour and then was extracted with ethyl acetate. The ethyl acetate extract was evaporated to dryness under vacuum. The residue was precipitated from an acetone-water solution to give 378 mg of A-28086 factor A sodium salt, melting point 120°-123° C.

EXAMPLES 11-15

Antibiotic A-28086 factor A barium salt was prepared from antibiotic A-28086 factor A (500 mg) and saturated barium hydroxide, using the method of Example 10 to give 369 mg of A-28086 factor A barium salt, melting point 188°-190° C.

Antibiotic A-28086 factor A potassium salt was prepared from antibiotic A-28086 factor A (500 mg) and 5 N potassium hydroxide, using the method of Example 10 to give 363 mg of A-28086 factor A potassium salt, melting point 165°-167° C.

Antibiotic A-28086 factor A cesium salt was prepared from antibiotic A-28086 factor A (500 mg) and 1 N cesium hydroxide, using the method of Example 10 to give 540 mg of A-28086 factor A cesium salt, melting point 190°-210° C.

Antibiotic A-28086 factor B sodium salt, prepared from antibiotic A-28086 factor B and 5 N sodium hydroxide according to the method of Example 10.

EXAMPLE 16

Shake-flask Fermentation of A-28086 using *S. aureofaciens* NRRL 8092

A culture of *Streptomyces aureofaciens* NRRL 8092 was prepared and maintained on an agar slant having the following composition:

| Ingredient | Amount |
| --- | --- |
| $K_2HPO_4$ | 2 g |
| $MgSO_4 . 7H_2O$ | 0.25 g |
| $NH_4NO_3$ | 2 g |
| $CaCO_3$ | 2.5 g |
| $FeSO_4 . 7H_2O$ | 0.001 g |
| $MnCl_2 . 7H_2O$ | 0.001 g |
| $ZnSO_4 . 7H_2O$ | 0.001 g |
| Glucose | 10 g |
| Agar | 20 g |
| Deionized water- | q.s. 1 liter |
| pH (unadjusted) | 7.7 |

The slant was inoculated with *Streptomyces aureofaciens* NRRL 8092, and the inoculated slant was incubated at 30° C. for about 7 days. The mature slant culture was covered with sterile beef serum and was scraped with a sterile loop to prepare a spore and mycelial suspension from the slant culture. The resulting suspension was lyophilized into a maximum of six pellets.

One of the lyophile pellets thus prepared was used inoculate 50 ml of a vegetative medium having the following composition:

| Ingredient | Amount |
|---|---|
| Glucose | 20 g |
| Soybean flour | 15 g |
| Corn-steep liquor | 10 g |
| CaCO$_3$ | 2 g |
| Tap water | q.s. 1 liter |
| pH adjusted to pH 6.5 with dil NaOH | |

The inoculated vegetative medium, in a 250-ml Erlenmeyer flask, was incubated at 30° C. for 48 hours on a rotary shaker at 250 rpm with a 2-inch arc.

The incubated vegetative medium described above (0.5 ml, 1 percent) was used to inoculate 50 ml of a fermentation medium having the following composition:

| Ingredient | Amount |
|---|---|
| Tapioca dextrin* | 60.0 g |
| Enzyme-hydrolyzed casein** | 6.0 g |
| Enzymatic hydrolysate of casein*** | 2.0 g |
| CaCO$_3$ | 2.0 g |
| MgSO$_4$ . 7H$_2$O | 0.5 g |
| Blackstrap molasses | 15.0 g |
| Refined soybean oil | 5.0 ml |
| Tap water | q.s. 1 liter |
| pH (unadjusted) 6.6 | |

* Staley Dextrin No. 11, A.E. Staley Co, Decatur, Ill.
** Amber EHC, Amber Laboratories, Juneau, Wisc.
*** NZ Amine A, Sheffield Chemical Co., Norwich, N.Y.

EXAMPLE 17

Tank Fermentation of A-28086 using *S. aureofaciens* NRRL 8092

The initial procedure described in Example 16 for the shake-flask fermentation of A-28086 was also used for tank fermentation. In order to produce a larger volume of inoculum, 10 ml of the incubated vegetative medium was used to inoculate 400 ml of a second-stage vegetative medium having the same composition as that of the first vegetative medium. This second-stage medium, in a 2-liter Erlenmeyer flask, was incubated at 30° C. for 24 hours on a rotary shaker at 250 rpm with a two-inch arc.

This incubated second stage vegetative medium (800 ml) was used to inoculate 100 liters of sterile fermentation medium having the following composition:

| Ingredient | Amount |
|---|---|
| Tapioca dextrin* | 60.0 g/l. |
| Enzyme-hydrolyzed casein** | 6.0 g/l. |
| Enzymatic-hydrolysate of casein*** | 2.0 g/l. |
| CaCO$_3$ | 2.0 g/l. |
| MgSO$_4$ . 7H$_2$O | 0.5 g/l. |
| Blackstrap molasses | 15.0 g/l. |
| Refined soybean oil | 5.0 mg/l. |
| Tap water | q.s. 1 liter |

* Staley Dextrin No. 11, A.E. Staley Co., Decatur, Ill.
** Amber EHC, Amber Laboratories, Juneau, Wisc.
*** NZ Amine A, Sheffield Chemical Co., Norwich, N.Y.

The pH of the medium was 6.8 ± 0.1 after sterilization by autoclaving at 121° C. for 30 minutes at 15–20 pounds pressure. In a 165-liter fermentation tank the inoculated production medium was allowed to ferment for 10–12 days at 28 ± 1° C. The fermentation medium was aerated with sterile air at the rate of 0.4 volumes of air per volume of culture medium per minute. The medium was stirred with conventional agitators at 300 rpm.

EXAMPLE 18

Separation of the A-28086 Antibiotic Complex Produced by *S. aureofaciens* NRRL 8092

Whole fermentation broth (60 liters), obtained by the method described in Example 17, was adjusted to pH 3 by the addition of dilute HCl. The resulting solution was filtered using a filter aid (Hyflo Super-cel, a diatomaceous earth, Johns-Manville Products Corp.). The separated mycelial cake was extracted with 30 liters of methanol, adding 1.56 kg of NaHCO$_3$ to the extract with stirring. After separation of this extract, the mycelial cake was again extracted with another 30 liters of methanol. The two methanol extracts were combined and concentrated under vacuum to remove the methanol. The remaining aqueous solution (about 7 liters) was adjusted to pH 7.5 with dilute HCl. The resulting solution was extracted twice with ethyl acetate (7-liter portions). The ethyl acetate extracts were combined and concentrated under vacuum to give an oily residue. This oily residue was dissolved in 1500 ml of acetone. Water (1500 ml) was added to the acetone solution. The resulting solution was adjusted to pH 3 with dilute HCl and was stirred one hour. The precipitate which had formed was separated by filtration and then was dissolved in acetone (1500 ml); water (400 ml) was added to this solution. The resulting solution was allowed to stand for 16 hours for crystallization to occur. The crystals formed were separated by filtration and dried under vacuum to give 74 g crude crystalline product containing A-28086 factors A and D and other crystalline impurities.

This crude crystalline product (40 g) was dissolved in about 250 ml of benzene. The benzene solution was then applied to a silica-gel column (9- × 120-cm column; Grace-Davidson grade 62 silica gal). The column was eluted successively with 40 liters of each of the following:
1. benzene
2. benzene:ethyl acetate (9:1)
3. benzene:ethyl acetate (4:1)
4. benzene:ethyl acetate (7:3)
5. benzene:ethyl acetate (1:1)
6. ethyl acetate
7. methanol One-liter fractions were collected. Each fraction was checked by assay against *Bacillus subtilis* and by thin-layer chromatography to identify the eluted compounds. A-28086I was eluted with benzene:ethyl acetate (4:1). A-28086 factor B was eluted with benzene:ethyl acetate (7:3). A-28086 factors A and D were eluted in the fractions obtained with benzene:ethyl acetate (7:3 and 1:1), fractions 119–156. These fractions were combined and evaporated to dryness under vacuum. The residue thus obtained was dissolved in acetone (500 ml). Water (500 ml) was added to the acetone solution, and the resulting solution was adjusted to pH 3 with dilute HCl and was stirred for one hour. The precipitate which formed was separated by filtration and was crystallized from acetone (500 ml)-water (180 ml). The crystals thus formed were separated by filtration and dried under vacuum to give 20.1 g of a mixture of A-28086 factors A and D.

EXAMPLE 19

Separation and Purification of Individual Factors A and D

The crystalline mixture of A-28086 factors A and D obtained in Example 18 (18.8 g) was dissolved in benzene (50 ml). The benzene solution was applied to a silica-gel column (7- × 100-cm column; E. Merck grade 60 silica gel, finer than 230 mesh ASTM). The column was eluted, at a flow rate of 90 ml per hour, successively with:
1. 12 liters of benzene
2. 12 liters of benzene:ethyl acetate (9:1)
3. 12 liters of benzene:ethyl acetate (4:1)
4. 32 liters of benzene:ethyl acetate (7:3)
5. 10 liters of methanol Thin-layer cellulose chromatography (Merck Darmstadt cellulose on aluminum support) was followed by *B. subtilis* bioautography to monitor the elution procedure. The following solvent system was used: water:methanol:acetone (12:3:1), adjusting the solution first to pH 10.5 with $NH_4OH$ and then to pH 7.5 with HCl.

One- to two-liter fractions were collected until activity was detected; then 200-ml fractions were collected. The fractions containing only A-28086 factor D were combined and evaporated under vacuum to a residue. This residue crystallized from acetone-water (1:1). The crystals were separated and dried under vacuum to give 140 mg of crystalline A-28086 factor D.

The fractions containing A-28086 factor D with a trace of A-28086 factor A were treated in the same manner to give an additional 150 mg of crystalline A-28086 factor D containing a small amount of A-28086 factor A.

The fractions containing only A-28086 factor A were also treated in the same manner to give 4.7 g of crystalline A-28086 factor A.

EXAMPLE 20

The A-28086 antibiotics were produced according to the process of Example 16, but using a slant medium having the following composition:

| Ingredient | Amount |
| --- | --- |
| Beef extract | 2.00 g |
| Dextrin | 20.00 g |
| Yeast extract | 2.00 g |
| Enzymatic-hydrolysate of casein | 4.00 g |
| $CoCl_2 \cdot 6H_2O$ | 0.02 g |
| Agar | 20.00 g |
| Deionized water | q.s. 1 liter |
| pH adjusted to 7.0 with KOH | | and incubating the inoculated slant at 28° C. for about 7 days.

EXAMPLE 21

The A-28086 antibiotics were produced according to the process of Example 17, but using a flask/production medium having the following composition:

| Ingredient | Amount |
| --- | --- |
| Tapioca dextrin* | 80 g/l. |
| Enzyme-hydrolyzed casein** | 15.0 g/l. |
| Blackstrap molasses | 15.0 g/l. |
| Calcium carbonate | 2.0 g/l. |
| Ammonium sulfate | 1.0 g/l. |
| Magnesium sulfate | 0.5 g/l. |

-continued

| Ingredient | Amount |
| --- | --- |
| Refined soybean oil | 4.6 g/l. |

*Staley Dextrin No. 11, A.E. Staley Co., Decatur, Ill.
**Amber EHC, Amber Laboratories, Juneau, Wisc.

EXAMPLE 22

The A-28086 antibiotics were produced according to the process of Example 21, but using an intermediate third-stage vegetative medium having the following composition:

| Ingredient | Amount |
| --- | --- |
| Cerelose | 20.0 g/l. |
| Corn-steep liquor (wet wt.) | 10.0 g/l. |
| Soybean grits | 15.0 g/l. |
| $CaCO_3$ | 2.0 g/l. |
| Yeast | 2.0 g/l. |
| Beet molasses | 5.0 g/l. |

EXAMPLE 23

A-28086-Modified Chick Ration for Coccidiosis Control

A balanced, high-energy ration adapted to feed chicks for rapid weight gain is prepared by the following recipe:

| Ingredient | % | lbs |
| --- | --- | --- |
| Ground yellow corn | 50 | 1,000 |
| Soybean meal, solvent-extracted dehulled, finely ground, 50 percent protein | 31.09 | 621.8 |
| Animal fat (beef tallow) | 6.5 | 130 |
| Dried fish meal, with solubles (60% protein) | 5.0 | 100 |
| Distillers' solubles from corn | 4.0 | 80 |
| Dicalcium phosphate, feed grade | 1.8 | 36 |
| Calcium carbonate | 0.8 | 16 |
| Vitamin premix (representing vitamins A, D, E, K, and $B_{12}$, choline, niacin, pantothenic acid, riboflavin, biotin, with glucose bulking agent) | 0.5 | 10 |
| Trace mineral premix (representing $MnSO_4$, ZnO, KI, $FeSO_4$, $CaCO_3$) | 0.2 | 4 |
| 2-Amino-4-hydroxybutyric acid (hydroxy analog of methionine) | 0.1 | 2 |
| A-28086 Factor A | 0.01 | 0.2 |

These substances are mixed in accordance with standard feed-mixing techniques. Chicks fed such a ration, with water ad libitum, are protected against exposure to coccidiosis; weight gains are comparable to those of coccidiosis-free chicks fed a similar, unmedicated diet.

EXAMPLE 24

A-28086-Improved Beef-Cattle Ration

A balanced high-grain beef-cattle ration is prepared as follows:

| Ingredient | % | lbs |
| --- | --- | --- |
| Finely ground corn | 67.8 | 1356 |
| Ground corn cob | 10 | 200 |
| Dehydrated alfalfa meal, | | |

| Ingredient | % | lbs |
|---|---|---|
| 17 percent protein | 5 | 100 |
| Dehulled soybean meal, solvent extracted, | | |
| 50 percent protein | 9.9956 | 199.912 |
| Cane molasses | 5 | 100.0 |
| Urea | 0.6 | 12.0 |
| A-28086 Factor A | 0.0044 | 0.088 |
| Dicalcium phosphate, feed grade | 0.5 | 10.0 |
| Calcium carbonate | 0.5 | 10.0 |
| Sodium chloride | 0.3 | 6.0 |
| Trace mineral premix | 0.03 | 0.6 |
| Vitamin A and $D_2$ premix* | 0.07 | 1.4 |
| Vitamin E premix** | 0.05 | 1.0 |
| Calcium propionate | 0.15 | 3.0 |

*Containing per pound: 2,000,000 I.U. of vitamin A; 227,200 I.U. of vitamin $D_2$ and 385.7 g of soybean feed with 1% oil added
** Corn distillers dried grains with solubles containing 20,000 I.U. of d-alpha-tocopheryl acetate per pound The mixed feed is compressed into pellets. At an average daily ingestion rate of 15 pounds of feed per animal, this feed supplies approximately 300 mg of A-28086 factor A per animal per day.

We claim:

1. A method of preventing or treating coccidiosis in poultry which comprises administering to poultry an effective anticoccidial amount of a composition comprising a physiologically-acceptable carrier and a compound selected from the group consisting of antibiotic A-28086 factor A which is a white crystalline compound when crystallized from acetone-water; which is soluble in lower alcohols, dimethylformamide, dimethyl sulfoxide, ethyl acetate, chloroform, acetone, and benzene; but which is only slightly soluble in hexane; and is insoluble in water; which melts at about 98°–100° C., resolidifies, and remelts at about 195°–200° C. and which has:
  a. a molecular weight of 764, as determined by mass spectrometry;
  b. an approximate elemental composition of 66.69 percent carbon, 9.85 percent hydrogen, and 23.10 percent oxygen;
  c. an empirical formula of $C_{43}H_{72}O_{11}$, as determined by mass spectrometry;
  d. a specific rotation of $-54°$ (c=0.2, methanol) when determined at 25° C.;
  e. an infrared absorption spectrum in chloroform with the following distinguishable absorption maxima: 2.85, 3.34, 5.83, 6.82, 7.22, 7.53 (weak), 7.78 (weak), 8.75 (strong), 8.95 (strong), 9.15, 9.50 (strong), 9.55 (strong), 9.60, 9.85, 10.15, 10.45, and 10.70 (weak) microns;
  f. in its ultraviolet spectrum in ethanol only end absorption below 220 m$\mu$;
  g. a nuclear magnetic resonance spectrum in deuterochloroform with the following characteristics: $\delta$6.01, 4.21, 4.11, 3.99, 3.89, 3.80, 3.67, 3.65, 3.57, 3.55, 2.83, 2.76, 2.74, 2.68, 2.66, 2.58, 2.56, 2.30, 2.22, 2.17, 2.10, 2.05, 1.96, 1.90, 1.85, 1.70, 1.62, 1.60, 1.47, 1.39, 1.31, 1.25, 1.18, 0.95, 0.93, 0.90, 0.88, 0.85, 0.77, 0.75, 0.73, 0.68, and 0.66 ppm;
  h. a titratable group with a p$K_a$ value of 7.9 in 80% aqueous dimethylformamide;
  i. a characteristic X-ray powder diffraction pattern ($Cu^{++}$ radiation, 1.5405 $\lambda$, nickel filter) having the following interplanar spacings in angstroms (d):

| d | Relative Intensity |
|---|---|
| 12.00 | 100 |
| 10.10 | 50 |
| 9.25 | 90 |
| 8.00 | 40 |
| 7.50 | 15 |
| 6.92 | 90 |
| 6.40 | 40 |
| 5.98 | 05 |
| 5.68 | 15 |
| 5.20 | 40 |
| 4.98 | 40 |
| 4.62 | 40 |
| 4.21 | 20 |
| 3.48 | 10 | j. an $R_f$ value of 0.24 on thin-layer chromatography over silica gel in a benzene-ethyl acetate (3:2) solvent system, using Bacillus subtilis ATCC 6633 as the detection organism;
  k. the following $R_f$ values in the paper-chromatographic systems indicated below, using Bacillus subtilis ATCC 6633 as detection organism:

| $R_f$ Value | Solvent System |
|---|---|
| 0.11 | Water saturated with methyl isobutyl ketone (MIBK) |
| 0.41 | Water saturated with MIBK plus 2% p-toluenesulfonic acid and 1% piperidine |
| 0.54 | Water:methanol:acetone (12:3:1)-adjusted to pH 10.5 with $NH_4OH$ and then lowered to pH 7.5 with $H_3PO_4$ |
| 0.48 | 1% MIBK, 0.5% $NH_4OH$ in water |
| 0.15 | 17.4 g $K_2HPO_4$, 30 ml ethanol per liter of water |
| 0.24 | Benzene saturated with water |
| 0.24 | Water |
| 0.75 | Water:MIBK:ethyl acetate (98:1:1) | l. an acid function capable of forming salts and ester derivatives; and
  m. at least one hydroxyl group capable of esterification;

A-28086 factor A acetyl ester derivative which is a white crystalline compound (from acetone-water); which is soluble in methanol, ethanol, dimethylformamide, dimethyl sulfoxide, ethyl acetate, chloroform, acetone and benzene; is only slightly soluble in hexane; and is insoluble in water; which melts at about 100°–103° C.; and which has:
  a'. a molecular weight of about 807;
  b'. an elemental composition of 67.67 percent carbon, 8.71 percent hydrogen, and 23.13 percent oxygen;
  c'. an empirical formula of $C_{45}H_{74}O_{12}$;
  d'. an infrared spectrum in chloroform with the following observable absorption maxima: 2.85, 3.36, 3.38 (strong), 5.80, 6.83, 7.25, 7.52 (strong), 7.60 (weak), 7.80 (strong), 8.45 (strong), 8.80 (strong), 8.95 (strong), 9.10 (strong), 9.20, 9.63, 9.80 (strong), 10.12 (weak), 10.25 (weak), and 10.50 microns;
  e'. an ultraviolet spectrum showing only end absorption;
  f'. a nuclear magnetic resonance spectrum in which the carbinyl resonance is shifted downfield to approximately 5.3 ppm;
  g'. a titratable group with a p$K_a$ value of 8.5 in 80% aqueous dimethylformamide;

h'. an acid function capable of forming salts and ester derivatives;

A-28086 factor A propionyl ester derivative which is a white crystalline compound (from acetone-water); which is soluble in methanol, ethanol, dimethylformamide, dimethyl sulfoxide, ethyl acetate, chloroform, acetone, and benzene; is slightly soluble in hexane; and is insoluble in water; which melts at about 96°–98° C.; and which has:
- a''. a molecular weight of about 821;
- b''. an elemental composition of 66.06 percent carbon, 9.17 percent hydrogen, and 23.41 percent oxygen;
- c''. an empirical formula of $C_{46}H_{76}O_{12}$;
- d''. an infrared absorption spectrum in chloroform with the following observable absorption maxima: 2.85, 3.33, 3.38 (strong), 3.45 (strong), 5.75 (strong), 5.82, 6.81, 7.22, 7.30 (strong), 7.50 (weak), 7.60 (weak), 7.80, 8.43, 8.75 (strong), 8.90, 9.05, 9.15 (strong), 9.50 (strong), 9.63, 9.83 (weak), 10.05 (strong), 10.13, 10.20 (strong), 10.45, and 10.68 microns;
- e''. an ultraviolet spectrum showing only end absorption;
- f''. a nuclear magnetic resonance spectrum in which the carbinyl resonance is shifted downfield to approximately 5.3 ppm;
- g''. an acid function capable of forming salts and ester derivatives;

A-28086 factor A butyryl ester derivative which is a white crystalline compound (from acetone-water); which is soluble in methanol, ethanol, dimethylformamide, dimethyl sulfoxide, ethyl acetate, chloroform, acetone, and benzene; is slightly soluble in hexane; and is insoluble in water; which melts about 96°–98° C.; and which has:
- a'''. a molecular weight of about 835;
- b'''. an approximate elemental composition of 67.60 percent carbon, 9.41 percent hydrogen, and 22.99 percent oxygen;
- c'''. an empirical formula of $C_{47}H_{78}O_{12}$;
- d'''. an infrared spectrum in chloroform with the following observable absorption maxima: 2.89, 3.40, 3.45, 3.51, 5.85, 5.92 (strong), 5.97 (strong), 6.90, 7.30, 7.84 (weak), 8.55, 8.85 (weak), 9.01 (strong), 9.26, 9.76, 9.95, 10.31, and 10.64 microns;
- e'''. a nuclear magnetic resonance spectrum in which the carbinyl resonance is shifted downfield to approximately 5.3 ppm;
- f'''. an acid function capable of forming salts and ester derivatives;

A-28086 factor A valeryl ester derivative which is a white crystalline compound (from acetone-water); which is soluble in methanol, ethanol, dimethylformamide, dimethyl sulfoxide, ethyl acetate, chloroform, acetone, and benzene; is slightly soluble in hexane; and is insoluble in water; which melts at about 173°–175° C.; and which has:
- a''''. a molecular weight of about 849;
- b''''. an approximate elemental composition of 67.89 percent carbon; 9.50 percent hydrogen and 22.61 percent oxygen;
- c''''. an empirical formula of $C_{48}H_{80}O_{12}$;
- d''''. an infrared spectrum in chloroform with the following observable absorption maxima: 2.90, 3.40, 3.45, 3.51, 5.87, 5.92 (strong), 5.99 (strong), 6.91, 7.30, 7.69 (weak), 7.87 (weak), 8.16, 8.58, 8.85 (weak), 9.26, 9.76, 10.00 (weak), 10.31, and 10.64 microns;
- e''''. a nuclear magnetic resonance spectrum in which the carbinyl resonance is shifted downfield to approximately 5.3 ppm;
- f''''. an acid function capable of forming salts and ester derivatives;

A-28086 factor A caproyl ester derivative which is a white crystalline compound (from acetone-water); which is soluble in methanol, ethanol, dimethylformamide, dimethyl sulfoxide, ethyl acetate, chloroform, acetone, and benzene; is slightly soluble in hexane; and is insoluble in water; which melts at about 163°–167° C.; and which has:
- a'''''. a molecular weight of about 863;
- b'''''. an approximate elemental composition of 68.18 percent carbon; 9.58 percent hydrogen; and 22.24 percent oxygen;
- c'''''. an empirical formula of $C_{49}H_{82}O_{12}$;
- d'''''. an infrared spectrum in chloroform with the following observable absorption maxima: 2.90, 3.40, 3.45, 3.51, 5.87, 5.92 (strong), 5.97 (strong), 6.90, 7.30, 7.66 (weak), 7.84 (weak), 8.16, 8.58, 8.85 (weak), 9.05 (strong), 9.17, 9.72, 9.95, 10.29, and 10.62 microns;
- e'''''. a nuclear magnetic resonance spectrum in which the carbinyl resonance is shifted downfield to approximately 5.3 ppm;
- f'''''. an acid function capable of forming salts and ester derivatives;

the pharmaceutically-acceptable salts of A-28086 factor A;

antibiotic A-28086 factor B, a white crystalline compound when crystallized from acetone-water, which is soluble in lower alcohols, dimethylformamide, dimethyl sulfoxide, ethyl acetate, chloroform, acetone and benzene; but which is only slightly soluble in hexane and is insoluble in water; and which has:
- a. a melting point of about 150°–153° C.;
- b. a molecular weight of 762, as determined by high resolution mass spectrometry;
- c. an empirical formula of $C_{43}H_{70}O_{11}$, as determined by high-resolution mass spectrometry;
- d. an infrared absorption spectrum in chloroform with the following distinguishable absorption maxima: 2.82, 3.30, 5.77, 5.85, 6.80, 7.20, 7.50 (weak), 7.72 (weak), 7.80 (weak), 8.57 (strong), 8.68, 8.90 (strong), 9.10, 9.50, 9.83 (strong), 9.90, 10.10, 10.17 (strong), 10.43 (weak), 10.80 (weak), 11.20 (weak), 11.35 (weak), 11.73 (weak), and 12.03 (weak) microns;
- e. an observed absorption maximum in ethanol in its ultaviolet spectrum at 220 m$\mu$ ($E_{1cm}^{1\%}$ =137.5, $\epsilon$=10.477);
- f. a nuclear magnetic resonance spectrum in deuterochloroform with the following characteristics: $\delta$7.20, 7.09, 6.26, 6.15, 4.19, 4.12, 4.05, 3.95, 3.89, 3.78, 3.62, 3.59, 3.52, 3.48, 2.81, 2.73, 2.63, 2.54, 2.52, 1.99, 1.91, 1.84, 1.71, 1.67, 1.64, 1.55, 1.43, 1.33, 1.18, 1.11, 0.96, 0.94, 0.90, 0.87, 0.84, 0.77, 0.74, and 0.68 ppm;
- g. an $R_f$ value of 0.42 on thin-layer chromatography over silica gel in benzene-ethyl acetate (3:2), using *Bacillus subtilis* ATCC 6633 as the detection organism;
- h. the following $R_f$ values in the paper-chromatographic systems indicated below, using *Bacillus subtilis* ATCC 6633 as the detection organism:

| R,Value | Solvent System |
|---|---|
| 0.16 | Water saturated with MIBK plus 2% p-toluenesulfonic acid and 1% piperidine |
| 0.46 | Water:methanol:acetone (12:3:1)- adjusted to pH 10.5 with NH$_4$OH and then lowered to pH 7.5 with H$_3$PO$_4$ |
| 0.36 | 1% MIBK, 0.5% NH$_4$OH in water |
| 0.51 | Benzene saturated with water |
| 0.11 | Water |
| 0.61 | Water:MIBK:ethyl acetate (98:1:1) | i. an acid function capable of forming salts and ester derivatives;
j. two ketone moieties; and
k. at least one hydroxyl moiety;
and the pharmaceutically-acceptable salts of A-28086 factor B.

2. The method of claim 1 wherein the carrier is a poultry feed.

3. The method of claim 1 in which the A-28086 compound is A-28086 factor A.

4. The method of claim 3 wherein the carrier is a poultry feed.

* * * * *

UNITED STATES PATENT AND TRADEMARK OFFICE
CERTIFICATE OF CORRECTION

PATENT NO. : 4,035,481

DATED : July 12, 1977

INVENTOR(S) : David H. Berg, Robert L. Hamill, Marvin M. Hoehn

It is certified that error appears in the above-identified patent and that said Letters Patent are hereby corrected as shown below:

Column 1, line 25, "improvied" should read -- improved --; line 45, "and" should read -- an --.

Column 2, line 29, "NRR1" should read -- NRRL --.

Column 3, line 66, "6,82" should read -- 6.82 --.

Column 4, line 16, "a" should read -- A --.

Column 5, line 52, "keton" should read -- ketone --.

Column 9, line 45, "antibotic" should read -- antibiotic --.

Column 12, line 36, "(w)" should read -- (W) --.

Column 13, line 14, there should be a period after "growth".

Column 14, line 32, "fiar" should read -- fair --.

Column 16, line 59, there should be a period after "employed".

Column 20, line 24, remove the comma after "ric"; add ® after "Autoturb"; line 33, add ® after "Autoturb".

Column 21, line 9, "!0" should read -- 10 --.

Column 22, Table VIII, there should be a line under "Controls    20    0    100    --    --".

Column 22, Table IX, there should be a line under "Infected Controls    --    0    63    1.60    --    36.32    --" and under "Infected Controls    --    0    65    1.3    --    3.24    --".

Columns 23 and 24, Table X continued, there should be a line under "Infected Controls    20    52    1.7    --    3.5    --".

Column 25, line 42, "*" should read --:--.

Column 27, line 51 in chart, delete "The inoculated vegetative medium, in a 250 ml".

Column 28, line 51, "10.1." should read -- 10 l. --.

UNITED STATES PATENT AND TRADEMARK OFFICE
CERTIFICATE OF CORRECTION

PATENT NO. : 4,035,481

DATED : July 12, 1977

INVENTOR(S) : David H. Berg, Robert L. Hamill, Marvin M. Hoehn

It is certified that error appears in the above-identified patent and that said Letters Patent are hereby corrected as shown below:

Column 31, line 1, add "to" at end of line.

Column 32, line 40, "gal" should read -- gel --.

Column 38, line 54, "$\epsilon$=10.477);" should read -- $\epsilon = 10,477);$ --

Signed and Sealed this

Thirtieth Day of October 1979

[SEAL]

Attest:

RUTH C. MASON
Attesting Officer

LUTRELLE F. PARKER
Acting Commissioner of Patents and Trademarks